(12) United States Patent
Hartsel et al.

(10) Patent No.: US 7,528,144 B2
(45) Date of Patent: May 5, 2009

(54) MOLECULES AND METHODS FOR FLUORESCENCE MICROSCOPY

(75) Inventors: Scott C. Hartsel, Eau Claire, WI (US); David E. Lewis, Eau Claire, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 415 days.

(21) Appl. No.: 10/906,956

(22) Filed: Mar. 14, 2005

(65) Prior Publication Data
US 2006/0205760 A1   Sep. 14, 2006

(51) Int. Cl.
*C07D 221/14* (2006.01)
*A61K 31/473* (2006.01)

(52) U.S. Cl. ........................... 514/290; 546/111
(58) Field of Classification Search ............ 546/111
See application file for complete search history.

(56) References Cited

U.S. PATENT DOCUMENTS

| 2,385,106 | A | * | 9/1945 | Scalera et al. ............... 546/100 |
| 5,235,045 | A |   | 8/1993 | Lewis et al. |
| 2002/0010279 | A1 | * | 1/2002 | Satcher et al. .............. 525/255 |

OTHER PUBLICATIONS

Parallel fluorescence detection of single biomolecules in microarrays by a diffractive-optical-designed 2×2 fan-out element. Blom H, Johansson M. 2002.*

Caplus English Abstract .DN 53:353, Yasuda Kazuo et al. See RN 101574-77-0 CAPLUS 1958.*

(Continued)

*Primary Examiner*—Rita J Desai
(74) *Attorney, Agent, or Firm*—Quarles & Brady LLP

(57) ABSTRACT

The present invention provides molecules and methods for fluorescent microscopy and visualization of biomolecules, such as cholesterol. In a preferred embodiment, the present invention provides a compound having the structure:

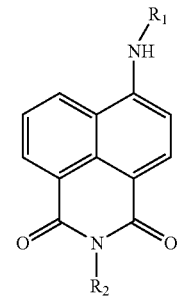

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8,
and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

2 Claims, 27 Drawing Sheets

OTHER PUBLICATIONS

Abuchowski, A., "Soluble Polymer-Enzyme Adducts," Enzymes as Drugs (J.S. Holcerberg and J. Roberts, eds. pp. 367-383 (1981)).

Brown, D.A., "Seeing is believing: Visualization of rafts in model membranes," PNAS 98:10517-8 (2001).

Buchwald, H., et al., "Long-term, continuous intravenous heparin administration by an implantable infusion pump in ambulatory partients. . . ," Surgery 88:507-516 (1980).

Chang, S.C., et al., "Snythesis and Bromination of 4-Alkylamino-N-alkyl-1, 8-naphthalimides," Dyes and Pigments 43:83-94 (1999).

Dietrich, C., et al., "Lipid Rafts Reconstituted in Model Membranes," Biophys. J., 80:1417-1428 (2001).

Goodson, J.M., "The Scope of Dental Therapy," Medical Applications of Controlled Release, supra, vol. II Applications and Evaluation, 115-138 (1984).

Gupta, N., et al., "Visualizing lipid raft dynamics and early signaling events during antigen receptor-mediated B-lymphoctye activation,"Mol. Bio. Cell 14:432-444 (2003).

Holtta-Vuori, M., et al., "Modulation of cellular cholesterol transport and Homeostatsis by Rab11," Mol. Biol. Cell 13:3107-3122 (2002).

Iwamoto, M., et al., "A biotinylated perfringolysin O derivative: a new probe for detection of cell surface cholesterol," Biochim. Biophys. Acta, 1327:222-230 (1997).

Jefferson, J.R., et al., "Intracellular sterol distribution in transfected mouse L-cell fibroblasts expressing rat liver fatty Acid . . . ," J. Biol. Chem. 266:5486-5496 (1991).

Katre, N.V., et al., "Chemical Modification of Recombinant Interleukin 2 by Polythylene Glycol Increases it Potency in the Murine . . . ,"Proc. Natl. Acad. Sci. USA 84:1487-1941 (1987).

Khan, T.K., et al., "Binding of NAP-22, a Calmodulin-Binding Neuronal Protein, to Raft-like Domains in Model Membranes," Biochemistry 42:4780-4786 (2003).

Langer, R., "New Methods of Drug Delivery," Science 249:1527-1533 (1990).

Langer, supra Sefton, CRC Crit. Ref. Biomed. Eng. 14:201 (1987).

Mundy, D.I., et al., "Dual Control of caveolar membrane traffic by microtubules and the actin cytoskeleton,"J. Cell Sci. 115:4327-4339 (2002)

Newmark, J., et al., "Preparation and properties of Adducts of Streptokinase and Streptokinase-Plasmin Complex with Polyethylene Glycol . . . ,"J. Appl. Biochem. 4:185-189 (1982).

Orlandi, P.A., et al., "Filipin-dependent Inhibition of Cholera Toxin: Evidence for Toxin Internalization and Activation through Caveolae-like Domains," J. Cell. Biol. 141:905-915 (1998).

Puri, V., et al., "Sphingolipid Storage Induces Accumulation of Intracellular Cholesterol by Stimulating SREBP-1 Cleavage," J. Biol. Chem. 278:20961-20970 (2003).

Puri, V., et al., "Cholesterol modulates membrane traffic along the endocytic pathway in sphingolipid-storage diseases," Nat. Cell Biol. 1:386-388 (1999).

Raju, T.N.K., "The Nobel Chronicles," Lancet 355:416 (2000).

Roff, C.F., et al., "Type C Niemann-Pick Disease: use of hydrophobic amines to study defective cholesterol transport." Dev. Neurosc. 13:315-319 (1991).

Sato, S.B. et al., "Distribution and transport of cholesterol-rich membrane domains monitored by a membrane-impermeant fluorescent polyethylene . . . ," J. Biol. Chem. 279:23790-23796 (2004).

Saudek, C.D., et al., "A Preliminary trail of the Programmable implantable Medication System for Insulin Delivery," N. Engl. J. Med. 321:574 (1989).

Schnitzer, J.E., et al., "Filipin-sensitive Caveolae-mediated Transport in Endothelium: Reduced Transcytosis, Scavenger Endocytosis, and Capillary . . . ," J. Cell Biol. 127:1217-1232 (1994).

Schroeder, F., et al., "Recent Advances in Membrane Microdomains: Rafts, Caveolae, and Intracellular Cholesterol Trafficking," Exp. Miol. Med. (Maywood) 226:873-890 (2001).

Scifinder Scholar Search Reports, Jul. 20, 2004.

Scifinder Scholar Search Reports, Jul. 21, 2004.

Sharma, D.K., et al., "Selective Stimulation of Caveolar Endocytosis by Glycosphingolipids and Cholesterol," Mol. Biol. Cell 15:3114-3122 (2004).

Shogomori, H., et al., "Cholesterol depletion by methyl-B-cyclodextrin blocks cholera toxin transport from endosomes to the Golgi apparatus . . . ," J. Neurochem. 78:991-999 (2001).

Singh, R.D., et al., "Selective Caveolin-1-dependent Endocytosis of Glycosphingolipids," Mol. Biol.. Cell, 14:3254-3265 (2003).

Sun, X., et al., "Niemann-Pick C Variant Detection by Altered Sphingolipid Trafficking and Correlation with Mutations within a Specific Domain . . . , " Am. J. Hum. Genet. 68:1361-1372 (2001).

Torgersen, M.L., et al., "Internalization of cholera toxin by different endocytic mechanisms," J. Cell Sci. 114:3737-3747 (2001).

Treat, J., et al., Liposomes in the Therapy of Infectious Disease and Cancer, Lopez-Berestein and Fidler (eds), Liss, NY 353-365 (1989).

Turtinen, L.W., et al., "Increased monokines in cytomegalovirus infected myelomonocytic cell cultures," Microb. Pathog. 7:135-145 (1989).

Watari, H., et al., "Niemann-Pick C-1 protein: obligatory roles for N-terminal domains and lysosomal targeting in cholesterol mobilization," Proc. Natl. Acad. Sci. USA 96:805-810 (1999).

* cited by examiner

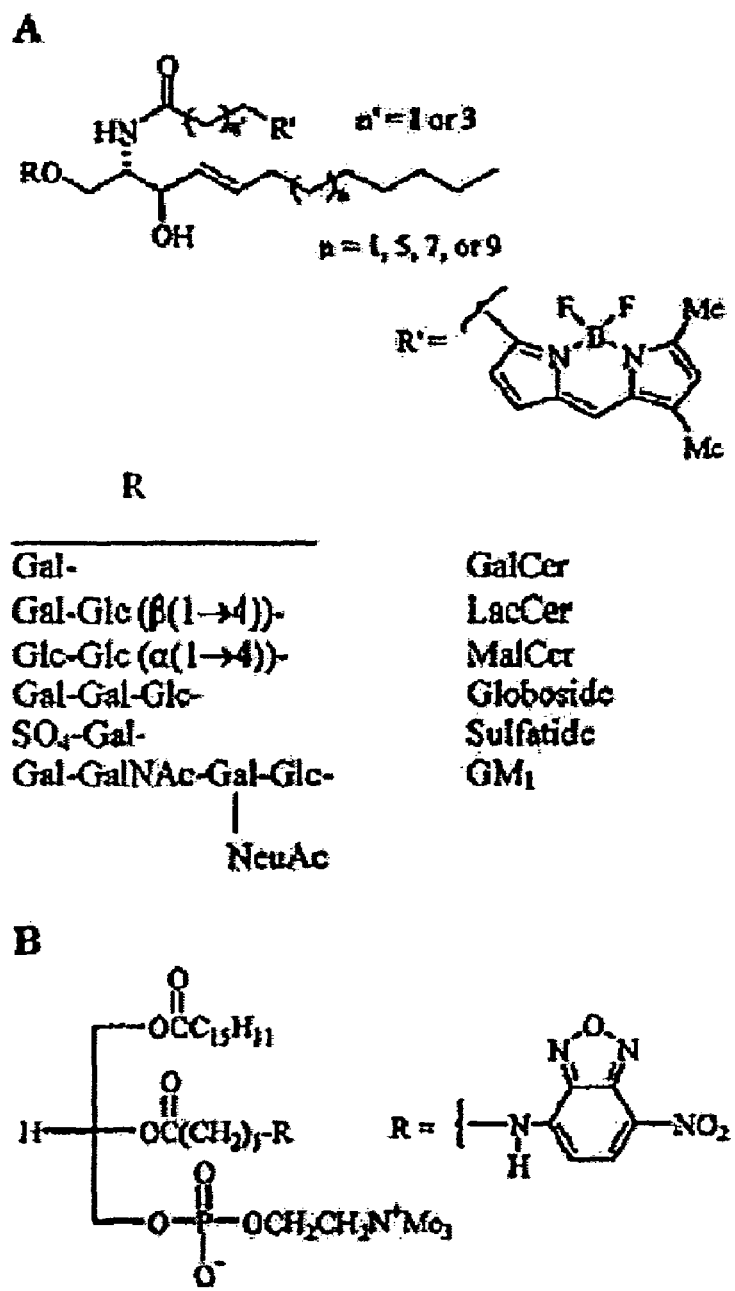

Figure 1. Structures of fluorescent lipid analogs used in the present study. (A) Various headgroups (R) were attached to BODIPY-ceramide, resulting in BODIPY-GalCer, -LacCer, -MalCer, -globoside, -sulfatide, or -GM₁. BODIPY-LacCer analogs were also synthesized using various chain length ($C_{12}, C_{14}, C_{16},$ or $C_{24}$) sphingosines or BODIPY-fatty acids ($C_5$ vs. $C_6$ spacer). Fluorescent LacCer bearing an NBD-fatty acid (see B) in place of the BODIPY-fatty acid was also synthesized. (B) Structure of the o-isomer of NBD-labeled PC, a glycerolipid.

FIG. 5

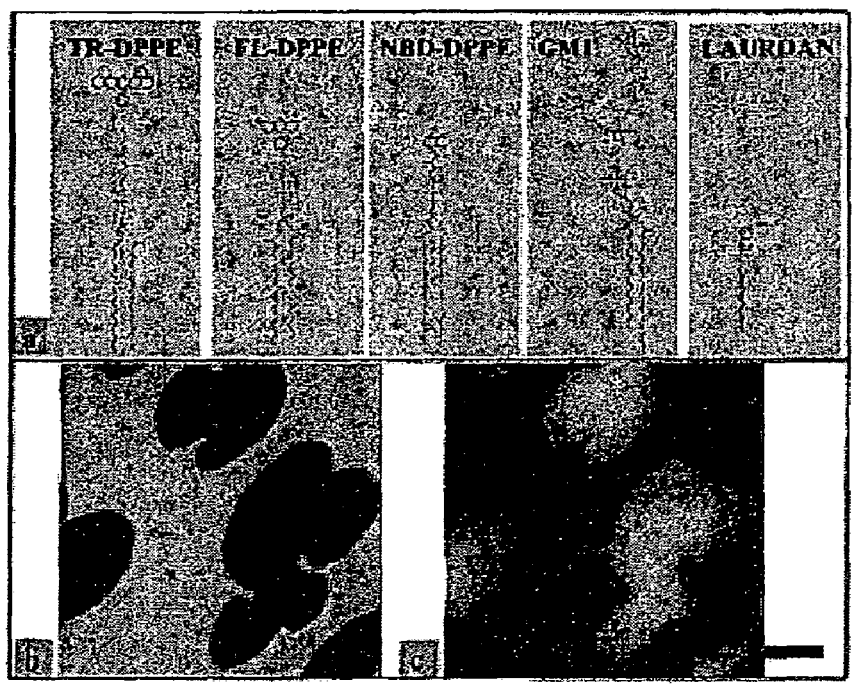

FIGURE 2 (a) Chemical structures of the various fluorescent lipid analogs employed and the glycosphingolipid, GM1; (b and c) Micrographs showing fluorescence of distal DPPC monolayer (with 0.5 mol % TR-DPPE and 1 mol % GM1) observed in deuterium channel (b) and fluorescein channel (c). The distal DPPC monolayer was deposited in the coexistence region for liquid and gel phases at 8 dyne/cm and 24°C from the water-air interface, to a proximal DPPC monolayer that was transferred previously to a glass coverslip at 32 dyne/cm. To stain GM1, the sample was incubated with FL-CTB (1 μg/ml in PBS) for 10 min. Bar, 20 μm.

FIG. 6

MOLECULES AND METHODS FOR FLUORESCENCE MICROSCOPY

TECHNICAL BACKGROUND

The present invention generally relates to molecules and methods for fluorescence microscopy and specifically relates to molecules such as InstantLyso LLT-1, InstantLipo Sep-1 and InstantGolgi McN-1 which are useful for fluorescence microscopy of biomolecules, such as cholesterol.

BACKGROUND

Cholesterol is the most decorated small molecule in biology[1], however, despite the wealth of knowledge of the biochemistry, biophysics and health-related effects of cholesterol, surprisingly little is known about the membrane trafficking of cholesterol in live cells[2]. This is likely due to a paucity of non-toxic, non-perturbing probes for cholesterol-rich domains.

Cholesterol-rich domains on cellular surfaces are often, but not exclusively, associated with caveolae, which are membrane invaginations for non-clathrin dependent endocytosis. These cholesterol and sphingolipid-rich domains are often referred to as lipid "rafts" and likely represent liquid-ordered phase regions of the membrane. There is currently a great deal of interest in the study of rafts and caveolar-mediated endocytosis because this pathway appears to be important in many disease states. Some processes associated with caveolae include binding and intracellular delivery and assembly of some bacterial toxins, binding and entry of viruses including HIV and bacteria as well as some growth factors and other circulating proteins [3, 4]. For example, seminal studies by Orlandi and Fishman [5] demonstrated that the cholera toxin B subunit (CtxB), which binds to the glycolipid $GM_1$ at the plasma membrane (PM), is internalized by caveolae in several cell types. More recent studies have shown that CtxB can also be significantly internalized by clathrin-dependent endocytosis in some cell types [6, 7]. Another potential marker for caveolar uptake is labeled serum albumin, which is reported to be internalized primarily by caveolae [8]. All of the pathways of cholesterol-related intracellular transport are still being investigated avidly, but a summary of the current state of the knowledge is shown in FIG. 4 and reviewed in [9].

Because of the growing realization of the importance of cholesterol-rich domains in cell biology, visualization of these domains has become a significant research area. There are various ways to visualize these domains in live and aldehyde-fixed cells. Some of pros and cons of these methods are summarized in Table 1 below. Some specific fluorescent sphingolipid analogs which have been used in live cells by Pagano's group and others for membrane vesicular trafficking studies are shown in FIG. 5. Other fluorescent probes which have been used in biophysical studies for delineating liquid/ordered lipid domains in model and cellular systems are shown in FIG. 6 [10, 11]. Brown[11] provides a concise summary of methods used for visualizing raft domains. The actual location of these probes is often ascertained by immunofluorescence colocalization with proteins "known" to be associated with certain domains (e.g. LAMP with lysosomes, caveolin with caveolae, clathrin with coated pits, GRASP65 and fluorescent ceramides with the Golgi apparatus and protein disulfide isomerase for the endoplasmic reticulum). Sometimes these assignments turn out to be controversial.

TABLE 1

Cholesterol and lipid raft microdomain detection in cells

1. Staining Methods:
    a. Cholera Toxin subunit B(CtxB)
        i. Binds to $GM_1$, associated with microdomains
        ii. Cells generally fixed, but can be used on live cells
        iii. Fluorescent CtxB is linked by antibodies to visualize/long expensive procedure
        iv. Not membrane permeable
    b. Dehydroergosterol
        i. UV excited/dim/photosensitive; a lot of autofluorescence interference
        ii. Difficult to deliver (e.g. cyclodextrin, albumin-complexed)
    c. Filipin III
        i. Toxic! Expensive! Cells must be fixed/UV excited
        ii. Membrane permeable/leads to membrane aggregates/precipitates
        iii. Rapidly photobleaches
        iv. Main cytological method to diagnose Niemann-Pick-C disease and visualize atherosclerotic plaques
    d. PEGylated-Fluorescent cholesterol
        i. Not membrane permeable
        ii. Useful for real-time endocytotic/caveolar trafficking studies
    e. Fluorescent Lipids
        i. May be used with live cells/membrane impermeant and insoluble (e.g. cyclodextrin, albumin carrier needed)
        ii. $GM_1$
        iii. Lac-Cer Sphingomyelin (BODIPY)
    f. Clostridium Toxin (Perfringolysin-O)/NAP-22
        i. Cells must be fixed
        ii. Not membrane permeable Accordingly, the need exists to improve studying cholesterol trafficking and liquid-ordered cholesterol-rich microdomains in real time. The need exists for simple, non-cytotoxic and fade-prone cholesterol binding agents with rapid intake by cells, even at very small concentrations. Molecules and methods are desirable such that they provide large Stoke's shift, high quantum yield and yet exhibit very little self-quenching properties.

SUMMARY OF THE INVENTION

The present invention provides molecules and methods for detecting biomolecules trough fluorescence microscopy. In a preferred embodiment, the present invention provides a compound having the structure:

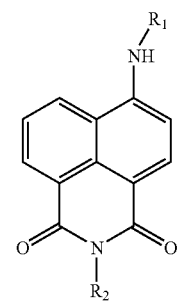

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$ wherein n has a value between 4 and 18, wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

Another embodiment of the present invention provides a method for detecting a biomolecule. The method comprises
(a) contacting a sample having or suspected of having a biomolecule with a compound having the structure:

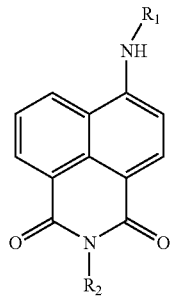

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

In this method, the biomolecule is selected from a group consisting of a lipid raft, sterol-binding protein, cholesterol, caveolin, liquid-ordered membrane domain, lysosome, Golgi apparatus, atherosclerotic plaque, cholesterol rich organelle and microtubule organizing center. The sample may be a live or a fixed cell. The detection of the biomolecule in the sample may be conducted by about 50 nM to about 500 nM of the compound. In a preferred embodiment, about 75 nM to about 200 nM of the compound is used for contacting the biomolecule. Detection of this biomolecule is preferably carried out through fluorescence microscopy which may be completed in about 15 seconds. In one embodiment, the detection is carried out in a wavelength range from about 200 nm to about 1000 nm. Preferably, the detection is carried out in a wavelength range from about 400 nm to about 600 nm.

Another embodiment of the present invention provides a method of detecting cholesterol trafficking or cholesterol rich domains. This method comprises:
(a) contacting a sample having or suspected of having a cholesterol with a compound having the structure:

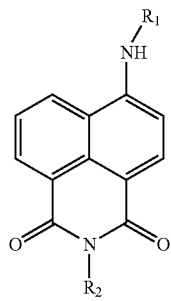

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

(b) detecting presence of the cholesterol through fluorescence microscopy.

As describe above, in this method the sample is a live or a fixed cell. The detection of cholesterol in the sample may be conducted by about 50 nM to about 500 nM of the compound. In a preferred embodiment, about 75 nM to about 200 nM of the compound is used for contacting the sample. Detection of this sample is preferably carried out through fluorescence microscopy which may be completed in about 15 seconds. In one embodiment, the detection is carried out in a wavelength range from about 200 nm to about 1000 nm. Preferably, the detection is carried out in a wavelength range from about 400 nm to about 600 nm.

Another embodiment of the present invention provides a pharmaceutical composition comprising:
(a) a compound having the formula:

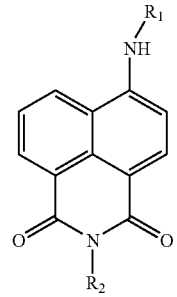

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl; or (b) a pharmaceutically acceptable salt of said compound; and (c) a pharmaceutically-acceptable carrier.

In this embodiment, the pharmaceutical composition is capable of detecting a biomolecule selected from a group consisting of a lipid raft, sterol-binding protein, cholesterol, caveolin, liquid-ordered membrane domain, lysosome, Golgi apparatus, atherosclerotic plaque, cholesterol rich organelle and microtubule organizing center.

The present invention also provides a kit for detecting a biomolecule. The kit comprises:
(a) a biomolecule sample;
(b) a detection apparatus; and
(c) a compound having the structure:

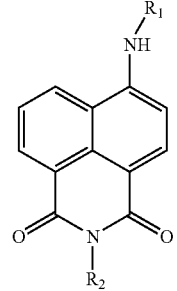

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$ wherein n has a value between 4 and 18,
wherein m has a value between 2 and 8,
and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

In this kit too, the sample may be a live or a fixed cell. About 75 nM to about 200 nM of the compound may be used for contacting with said biomolecule. The detection apparatus, in a preferred embodiment is a fluorescence microscope, capable of detecting fluorescence from wavelengths at least 400 nm wavelength to 600 nm.

Other objects and advantages of the present invention will be apparent from the detailed description, drawings and claims accompanying the specification

BRIEF DESCRIPTION OF THE DRAWINGS

FIG. 5 depicts Some specific fluorescent sphingolipid analogs which have been used in live cells for membrane vesicular trafficking studies.

FIG. 6 depicts fluorescent probes which have been used in biophysical studies for delineating liquid/ordered lipid domains in model and cellular systems.

DETAILED DESCRIPTION OF THE PREFERRED EMBODIMENT

A: General

Figure 1:
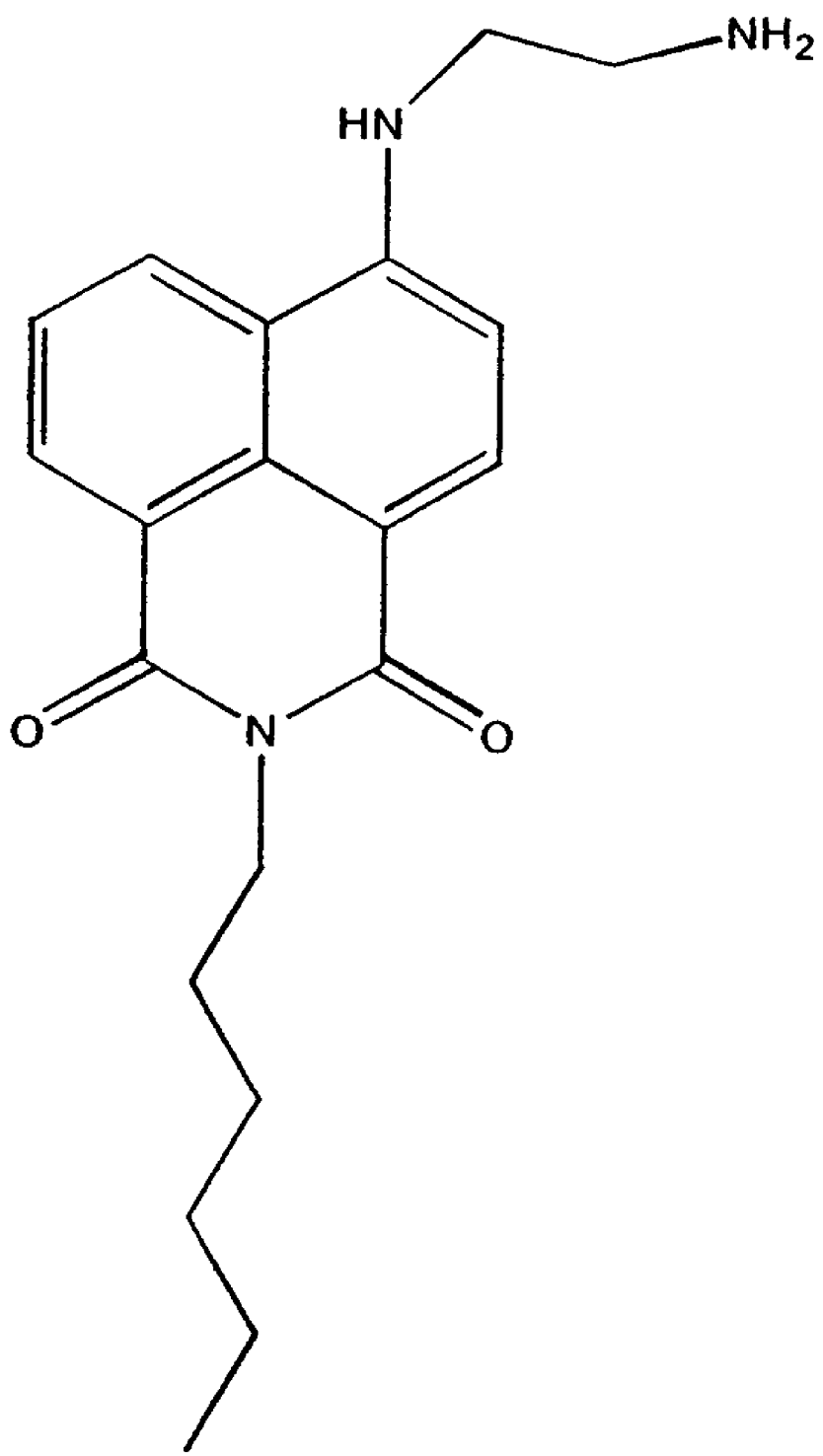
FIG. 1 depicts the structure of InstantLyso LLT-1 compound.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

B. Preferred Embodiments

The present invention provides molecules and methods for detecting biomolecules trough fluorescence microscopy. In a preferred embodiment, the present invention provides a compound having the structure:

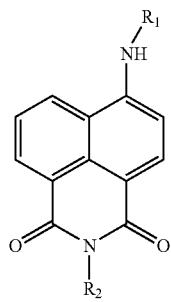

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8,
and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl.

In a more preferred embodiment, the present invention provides a compound having the structure:

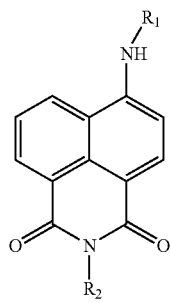

wherein $R_1$ is selected from the group consisting of H,

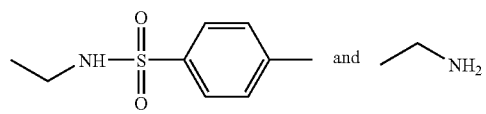

and wherein $R_2$ is selected from the group consisting of $C_6H_{13}$, $C_7H_{15}$ and $C_8H_{17}$.

Another embodiment of the present invention provides a method for detecting a biomolecule. The method comprises
(a) contacting a sample having or suspected of having a biomolecule with a compound having the structure:

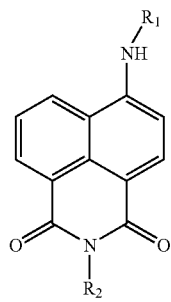

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$
wherein n has a value between 4 and 18,
wherein m has a value between 2 and 8,
and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl; and
(b) detecting presence of the biomolecule through fluorescence microscopy.

In this method, the biomolecule is selected from a group consisting of a lipid raft, sterol-binding protein, cholesterol, caveolin, liquid-ordered membrane domain, lysosome, Golgi apparatus, atherosclerotic plaque, cholesterol rich organelle and microtubule organizing center. The sample may be a live or a fixed cell. The detection of the biomolecule in the sample may be conducted by about 50 nM to about 500 nM of the compound. In a preferred embodiment, about 75 nM to about 200 nM of the compound is used for contacting the biomolecule. Detection of this biomolecule is preferably carried out through fluorescence microscopy which may be completed in about 15 seconds. In one embodiment, the detection is carried out in a wavelength range from about 200 nm to about 1000 nm. Preferably, the detection is carried out in a wavelength range from about 400 nm to about 600 nm. In a more preferred embodiment, the compound has the following structure:

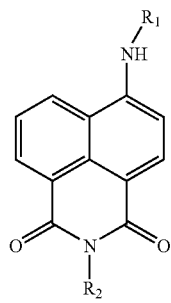

wherein $R_1$ is selected from the group consisting of H,

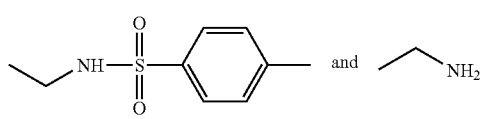

and wherein $R_2$ is selected from the group consisting of $C_6H_{13}$, $C_7H_{15}$ and $C_8H_{17}$.

Another embodiment of the present invention provides a method of detecting cholesterol trafficking or cholesterol rich domains. This method comprises:

(a) contacting a sample having or suspected of having a cholesterol with a compound having the structure:

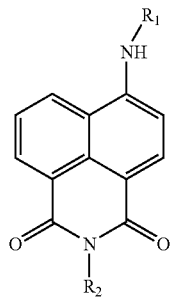

wherein $R_1$ and $R_2$ are selected from the group consisting of H, $C_nH_{2n+1}$, $(CH_2)_mNH_2$, $(CH_2)_mNH$—$SO_2$—R', and $CH_2CH_2OCH_2CH_2NH_2$
wherein n has a value between 4 and 18,
wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl; and (b) detecting presence of the cholesterol through fluorescence microscopy.

In a more preferred embodiment, the compound has the following structure:

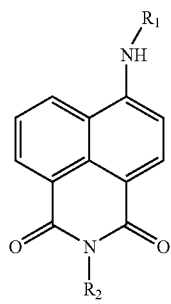

wherein $R_1$ is selected from the group consisting of H,

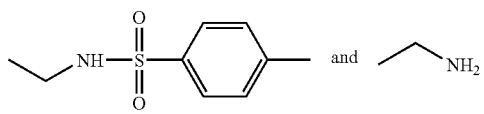

and wherein $R_2$ is selected from the group consisting of $C_6H_{13}$, $C_7H_{15}$ and $C_8H_{17}$.

As describe above, in this method the sample is a live or a fixed cell. The detection of cholesterol in the sample may be conducted by about 50 nM to about 500 nM of the compound. In a preferred embodiment, about 75 nM to about 200 nM of the compound is used for contacting the sample. Detection of this sample is preferably carried out through fluorescence microscopy which may be completed in about 15 seconds. In one embodiment, the detection is carried out in a wavelength range from about 200 nm to about 1000 nm. Preferably, the detection is carried out in a wavelength range from about 400 nm to about 600 nm.

Another embodiment of the present invention provides a pharmaceutical composition comprising:

(a) a compound having the formula:

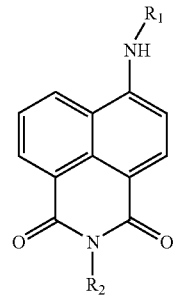

wherein $R_1$ and $R_2$ are selected from the group consisting of H, $C_nH_{2n+1}$, $(CH_2)_mNH_2$, $(CH_2)_mNH$—$SO_2$—R', and $CH_2CH_2OCH_2CH_2NH_2$
wherein n has a value between 4 and 18,
wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl; or (b) a pharmaceutically acceptable salt of said compound; and (c) a pharmaceutically-acceptable carrier. In a more preferred embodiment, the compound has the following structure:

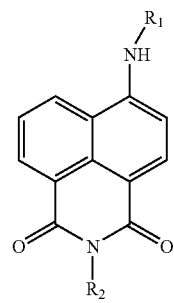

wherein $R_1$ is selected from the group consisting of H,

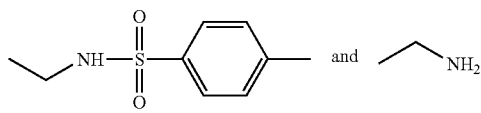

and wherein $R_2$ is selected from the group consisting of $C_6H_{13}$, $C_7H_{15}$ and $C_8H_{17}$.

In this embodiment, the pharmaceutical composition is capable of detecting a biomolecule selected from a group consisting of a lipid raft, sterol-binding protein, cholesterol, caveolin, liquid-ordered membrane domain, lysosome, Golgi apparatus, atherosclerotic plaque, cholesterol rich organelle and microtubule organizing center.

The present invention also provides a kit for detecting a biomolecule. The kit comprises:

(a) a biomolecule sample;
(b) a detection apparatus; and
(c) a compound having the structure:

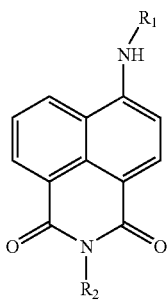

wherein $R_1$ and $R_2$ are selected from the group consisting of H, $C_nH_{2n+1}$, $(CH_2)_mNH_2$, $(CH_2)_mNH-SO_2-R'$, and $CH_2CH_2OCH_2CH_2NH_2$ wherein n has a value between 4 and 18, wherein m has a value between 2 and 8, and wherein R' is selected from the group consisting of $CH_3$, $C_6H_5$, $C_6H_4CH_3$, $C_6H_4CO_2H$ and its cyclic imide, $C_6H_4Br$, anthraquinon-2-yl, and 5-formyl-2-furyl, 2-carboxyphenyl. In a more preferred embodiment, the compound has the following structure:

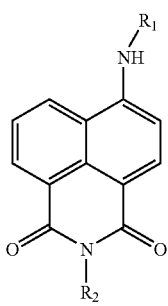

wherein $R_1$ is selected from the group consisting of H,

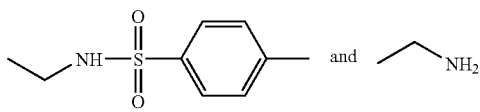

and wherein $R_2$ is selected from the group consisting of $C_6H_{13}$, $C_7H_{15}$ and $C_8H_{17}$.

In this kit too, the sample may be a live or a fixed cell. About 75 nM to about 200 nM of the compound may be used for contacting with said biomolecule. The detection apparatus, in a preferred embodiment is a fluorescence microscope, capable of detecting fluorescence from wavelengths at least 400 nm wavelength to 600 nm.

As defined herein, the term "compound" includes the above described structures and its pharmaceutically acceptable salts, metabolites, hydrates, isomers and derivatives.

As defined herein, the term "isomer" includes, but is not limited to optical isomers and analogs, structural isomers and analogs, conformational isomers and analogs, and the like. In one embodiment, this invention encompasses the use of different optical isomers of above described compound. It will be appreciated by those skilled in the art that the compounds useful in the present invention may contain at least one chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereroisomeric form, or mixtures thereof, which form possesses properties useful in the treatment of conditions described and claimed herein. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also he prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes method utilizing derivatives of the compound. The term "derivatives" includes but is not limited to ether derivatives, acid derivatives, amide derivatives, ester derivatives and the like. In addition, this invention further includes methods utilizing hydrates of the compound.

The term "hydrate" includes but is not limited to hemihydrate, monohydrate, dihydrate, trihydrate and the like.

This invention further includes methods of utilizing metabolites of the compounds. The term "metabolite" means any substance produced from another substance by metabolism or a metabolic process.

As defined herein, "contacting" means that the compound used in the present invention is introduced into a sample containing a sample having a receptor in a test tube, flask, tissue culture, chip, array, plate, microplate, capillary, or the like, and incubated at a temperature and time sufficient to permit binding of the compound to the receptor. Methods for contacting the samples with the compound or other specific binding components are known to those skilled in the art and may be selected depending on the type of assay protocol to be run. Incubation methods are also standard and are known to those skilled in the art.

In another embodiment, the term "contacting" means that the compound used in the present invention is introduced into a patient or a subject for detection of the biomolecule, and the compound is allowed to come in contact with the biomolecule in vivo.

A "patient" or "subject", used equivalently herein, refers to a mammal, preferably a human that has a biomolecule which is detectable by compounds of the present invention.

As used herein, "pharmaceutical composition" means therapeutically effective amounts of the compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active agent sufficient to yield a desired response without undue adverse side effects such as toxicity, irritation, or allergic response. The specific "effective amount" will, obviously, vary with such factors as the particular condition being treated, the physical condition of the patient, the type of animal being treated, the duration of the treatment or diagnosis, the nature of concurrent therapy (if any), and the specific formulations employed and the structure of the compounds or its derivatives. In this case, an amount would be deemed effective if it resulted in one or more of the following: (a) the detection of a desired biomolecule in vivo or/in vitro; and (b) the imaging of a desired biomolecule in vivo or/in vitro. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1 987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the compound can be administered to a subject by, for example, subcutaneous implantation of a pellet. In a further embodiment, a pellet provides for controlled release of the compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administerable by the invention can be prepared by known dissolving, mixing, granulating, or tablet-forming processes. For oral administration, the compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

Finally, for use in medicine, the salts of the compound may be pharmaceutically acceptable salts. Other salts may, however, be useful in the preparation of the compounds according to the invention or of their pharmaceutically acceptable salts.

Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The following Examples are offered by way of illustration and not by way of limiting the scope of the present invention.

EXAMPLES

Example 1

Synthesis of Modified Naphthalimide Dyes

The starting amines were prepared by the procedures given in Lewis, et. al., (Lewis, D. E.; Utecht, R. E.; Judy, M. M.; Matthews, J. L. "Non-Azo Naphthalimide Dyes." U.S. Pat. No. 5,235,045 [Aug. 10, 1993].), and in Chang, et. al. (Chang, S.-C.; Utecht, R. E.; Lewis, D. E. "Synthesis and Bromination of 4-Alkylamino-N-alkyl-1,8-naphthalimides." *Dyes and Pigments* 1999, 43, 83-94.). The methods used for making "InstantLyso LLT-1", "InstantGolgi McN-1", and "InstantLipo Sep-1" are described.

A. Synthesis of "LTT": 6-(2-aminoethyl)amino-2-hexyl-1H-benz[de]isoquinoline-1,3-(2H)-dione or 4-(2-aminoethyl)amino-N-hexyl-1,8-naphthalimide A stirred mixture of freshly recrystallized 4-chloro-1,8-naphthalic anhydride (4.68 g, 20 mmol, purchased from InstantLyso LLT-1 Acros Organics, Fisher Scientific) and 1-hexylamine (1.98 g, 20 mmol) in toluene (50 mL) was heated under reflux for 16 h, after which the solution was cooled. The pale yellow solid which precipitated was collected by vacuum filtration and recrystallized from ethanol to afford 4-chloro-N-hexyl-1,8-naphthalimide (5.52 g, 87%) as a pale yellow solid, m.p. 65-68° C. The spectroscopic and physical properties of this material were in accord with the literature values.

Subsequently, 4-Chloro-N-hexyl-1,8-naphthalimide (3.49 g, 11 mmol) was dissolved in ethylenediamine (50 mL), and the reaction mixture was stirred under reflux for 16 h. After this time, the solvent was removed by evaporation under reduced pressure to afford the crude product as a red oil. Recrystallization from methanol afforded the product (3.57 g, 94%) as an orange solid, m.p. 87-89° C. The analysis corresponds to the methanol hemi-solvate of the hemi-hydrochloride salt.

Found: C, 65.5; H, 7.4; N, 10.8; $C_{20}H_{25}N_3O_2$ requires C, 70.8; H,7.4; N, 12.4; $[C_{20}H_{25}N_3O_2]_2 \cdot HCl \cdot CH_3OH$ requires C, 65.9; H, 7.4; N, 11.2%.

InstantLyso LLT-1 is dissolved in DMSO to make a 1 mM working stock solution and is stored away from light at $\leq 20°$ C.

The structure of InstantLyso LLT-1 is shown in FIG. 1. InstantLyso LLT-1 $C_{20}O_2N_3H_{25}$ has an excitation/emission maximum at 421 nm/533 nm, has FW=339.44.

B. Synthesis of "InstantGolgi McN-1": N-hexyl-4-[2-(4-toluensulfonyl)aminoethyl]amino-1,8-naphthalimide:

To 4-(2-aminoethyl)amiono-N-hexyl-1,8 naphthalimide (0.40 g, 1.2 mmol) in dichloromethane (≈50 mL) was added p-toluenesulfonyl chloride (0.69 g, 3.6 mmol). The reaction mixture was allowed to stir 2 weeks at ambient temperature, during which time an orange solid was deposited. The orange solid (0.35 g, 60%) was collected by vacuum filtration, and washed with a little cold dichloromethane.

Figure 2:
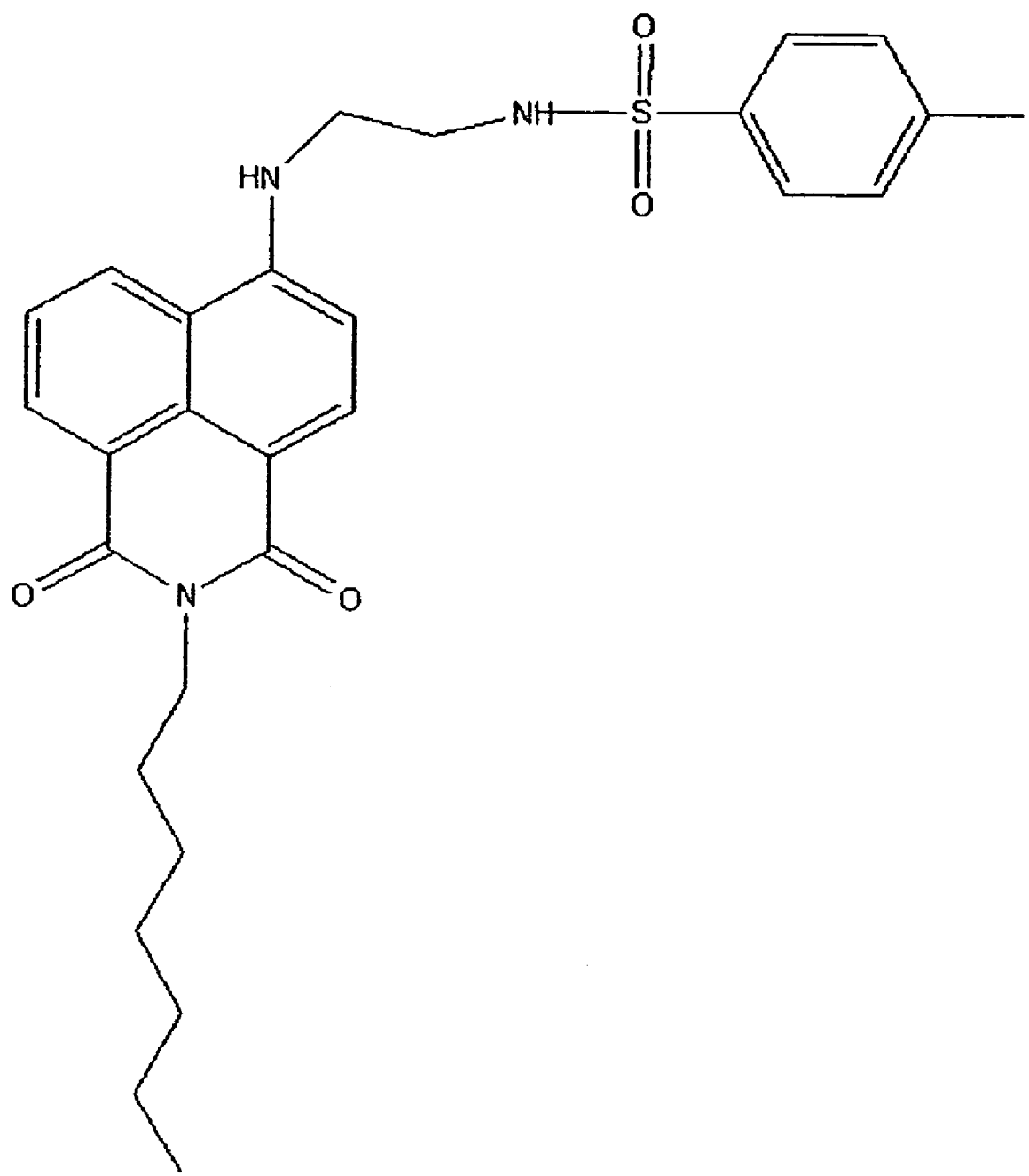
FIG. 2 depicts the structure of InstantGolgi McN-1 compound.
Figure 21:
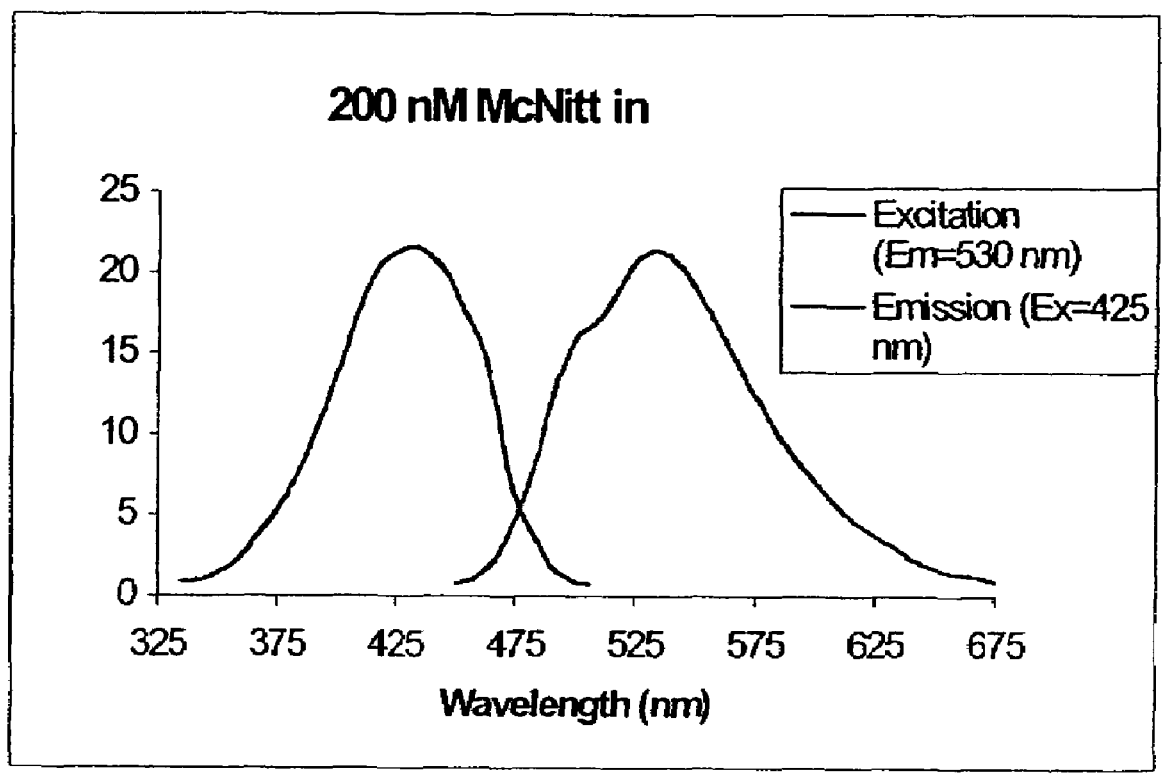
FIG. 21 depicts excitation and emission spectra for InstantGolgi McN-1 compound.

This reaction requires at least a two-fold molar quantity of the sulfonyl chloride relative to the amine. When the two reagents were used in the stoichiometric ratio, none of the expected product was obtained. The structure of InstantGolgi McN-1 is shown in FIG. 2. InstantGolgi McN-1 exhibits Em/Ex at 530/425nm, as seen in FIG. 21.

C. Synthesis of N-alkyl-4-amino-1,8-naphthalimides (e.g. "InstantLipo Sep-1").

These amines were prepared by the procedures given in Chang, et. al. (Chang, S.-C.; Utecht, R. E.; Lewis, D. E. "Synthesis and Bromination of 4-Alkylamino-N-alkyl-1,8-naphthalimides."*Dyes and Pigments* 1999, 43, 83-94.).

The synthesis of 4-amino-N-butyl-1,8-naphthalimide is representative:

A saturated solution of sodium methoxide in methanol was prepared by adding sodium metal (2.0 g, 0.87 mol) to methanol (10 mL) under reflux. This solution was added dropwise with stirring to a solution of 4-amino-1,8-naphthalimide (5.0 g, 24 mmol) in DMF (150 mL) under an inert atmosphere (nitrogen) until the red color persisted. Stirring was continued for another 15 minutes, at which time 1-bromobutane (13.11 g, 95 mmol) was added rapidly with stirring. The reaction mixture was stirred 1 hour in an ice-bath, and then poured into a mixture of ice and water ($\approx$1500 mL) and stirred for 1 hour. After this time, the orange-yellow solid precipitated as collected by vacuum filtration, and recrystallized from acetic acid-water to give the expected product (5.93 g, 94%), whose physical and spectroscopic characteristics correlated with an authentic sample.

Figure 3:
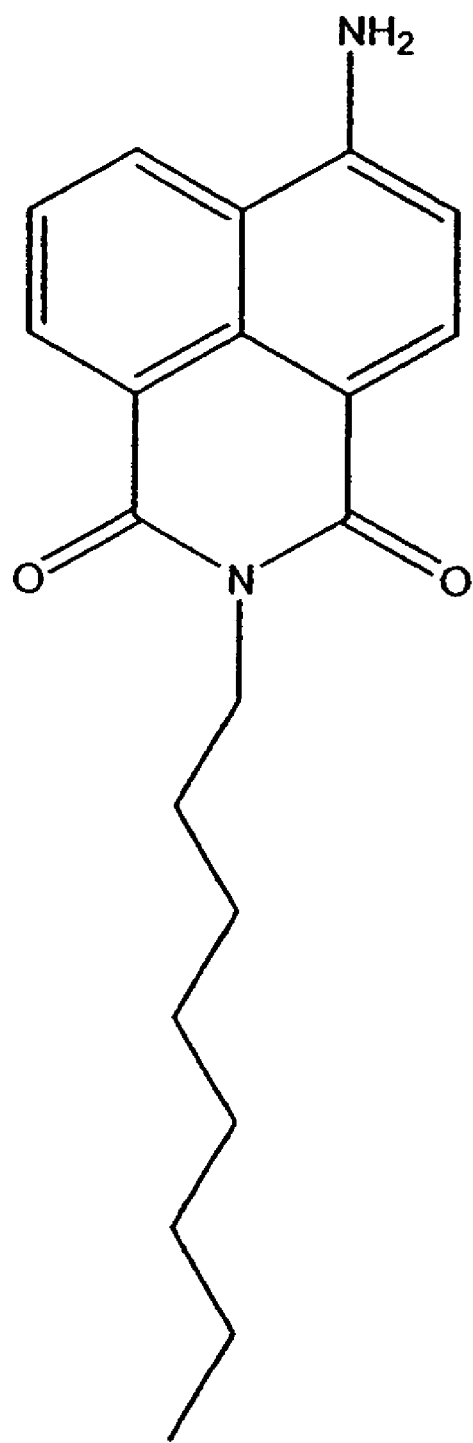
FIG. 3 depicts the structure of InstantLipo Sep-1compound.
Figure 4:
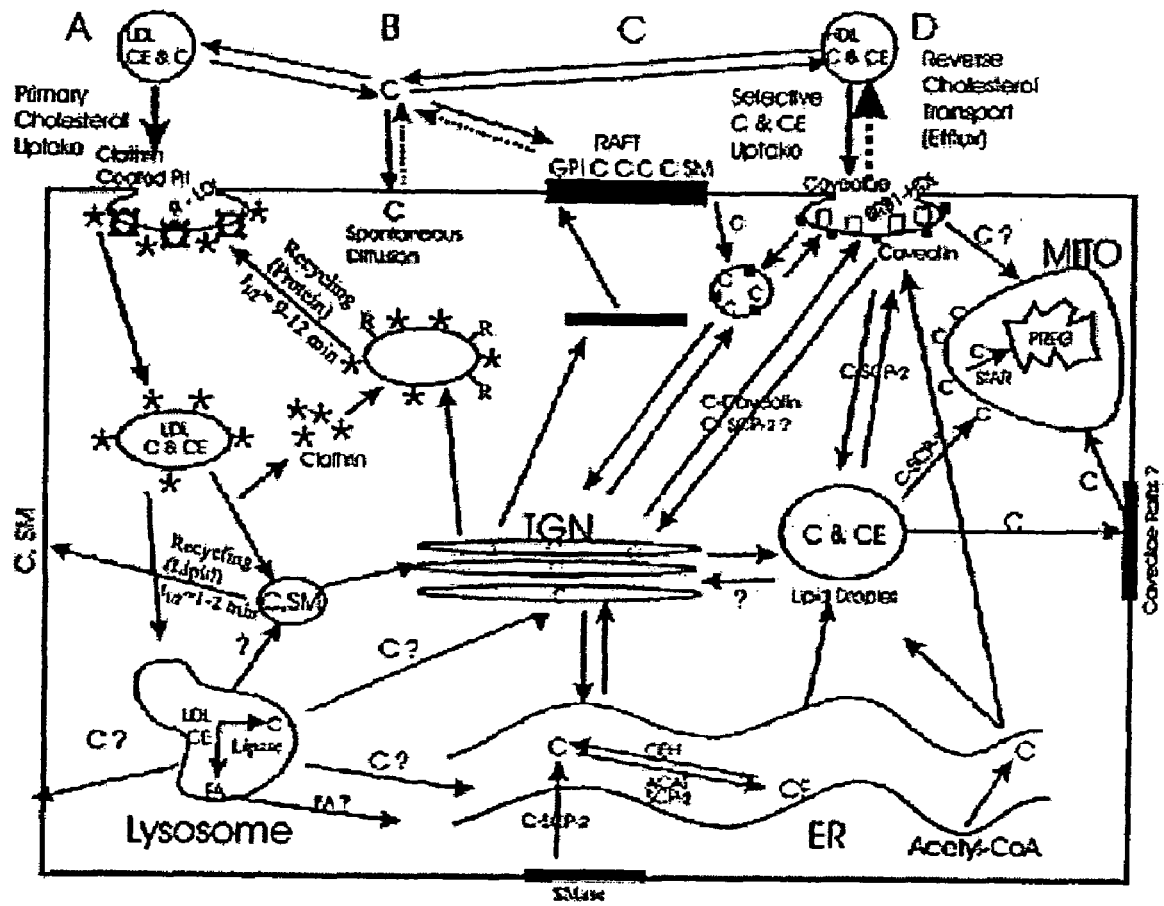
FIG. 4 depicts various pathways of cholesterol-related intracellular transport.
Figure 20:
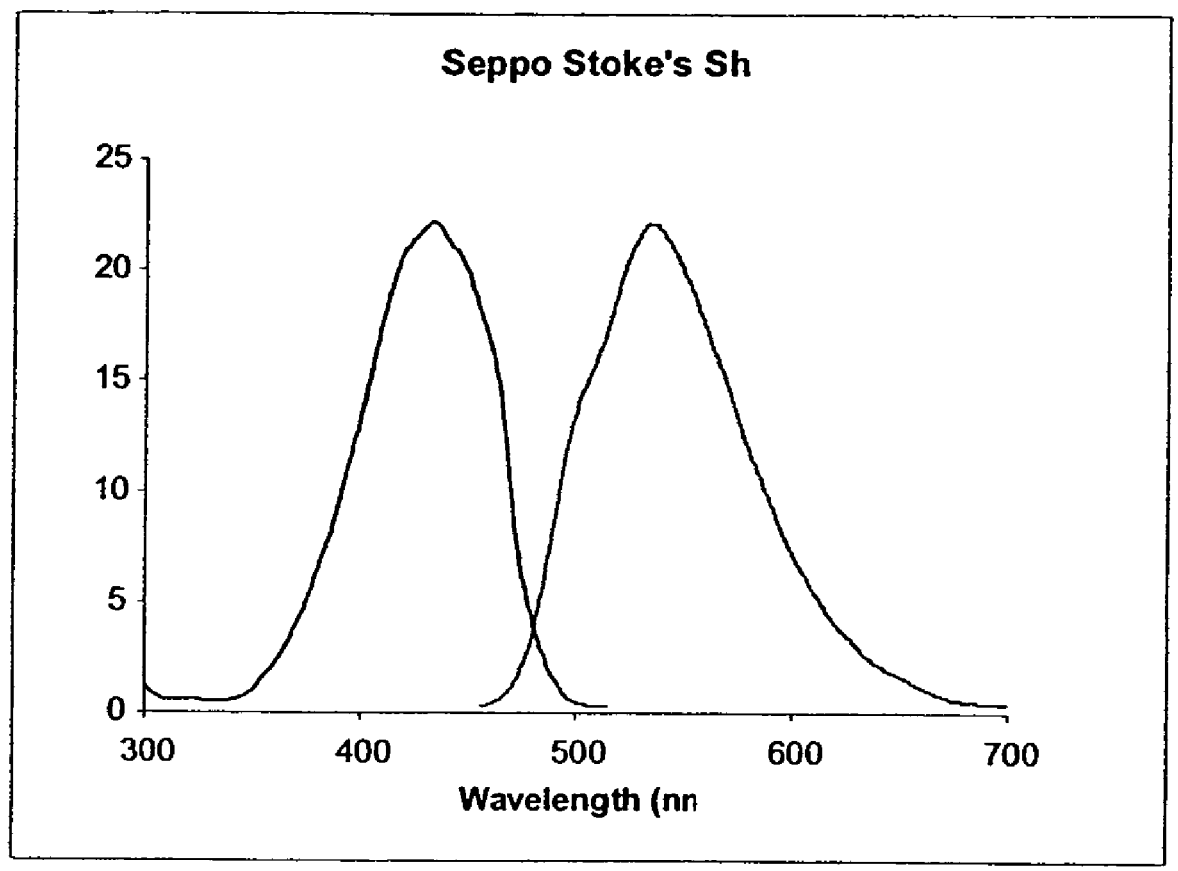
FIG. 20 depicts Stoke shift as seen in InstantLipo Sep-1compound.

InstantLipo Sep-1is dissolved in DMSO. The structure of InstantLipo Sep-1is shown in FIG. 3. The excitation/emission maximum is 433 nm/535 nm. The formula is $C_{20}H_{24}O_2N_2$, FW=324.42. InstantLipo Sep-1has a significant Stoke's shift as seen in FIG. 20.

Example 2

Cell Viability Studies

Cell culture for all studies. The THP-1 (monocytic leukemic, obtained from the ATCC line # TIB-202) cell line was grown at 37° C., 5% $CO_2$ to a saturation density of $1\times10^6$ cells/ml in RPMI medium containing 10 % endotoxin free fetal bovine serum (FBS), glutamine, 100 units/ml penicillin, 100 μg/ml streptomycin, 1 μg/ml gentamicin, and $2\times10^{-5}$ M β-mercaptoethanol as previously described in L. W. Turtinen, A. Assimacopoulos and A. T. Haase, Microb Pathog 7 (1989) 135-45. Cells were then harvested by pelleting in Eppendorf tubes at 1000×g for 10 minutes. Cells were counted using a hemacytometer. THP-1 cells in fresh medium were added to a sterile glass-bottomed polylysine coated 35 mm culture plates and incubated for 15 minutes ate 37° C. to promote adherence. Approximately 2 mL of warmed medium containing probe(s) was then added after adherence and aspiration of spent medium.

Human foreskin fibroblasts were grown as described above in Eagle's Minimum Essential Medium (EMEM) with 10% FBS in plastic tissue culture flasks and were removed from the flask when confluent by washing with calcium and magnesium free PBS followed by treatment with 0.05% trypsin/ 0.5 mM EDTA at 37° C. for 3-5 minutes. Split fibroblasts were grown in 60 mL culture dishes in EMEM in the presence of Hellmanex (1%)-washed coverslips for microscopic studies. In 4-5 days, cells were confluent on the coverslips for live/fixed staining. Cells were visualized by inversion of cover slip onto a silicone gasket on a microscope slide, forming a chamber containing medium. All cells were observed at ambient temperature.

For studies with fixed cells, a solution of 4% w/v paraformaldehyde in PBS containing 1% methanol was used. Cells were fixed at 37° C. for 10 minutes, then washed in PBS.

Microscopy: An Olympus B-MAX 60 microscope with Spot digital camera and green, UV, blue/purple and blue excitation filter sets or Olympus IX81 microscope, with corresponding confocal DSU (disc-spinning unit), filter sets and Hamamatsu camera were used for visualization of live and fixed cells. For the naphthalimide probes in both microscopic systems, a blue/purple filter cube was used (450/50 ex and 510/50 em with D480 mirror).

THP-1 Cell Viability Studies for naphthalimide probes. Trypan blue exclusion was used as an assay of cell viability in the presence of the various probes. THP-1 cells, >3 days old, were exposed to 100 nM LLT-1 or 200 nM InstantLipo Sep-1in RPMI 1640 medium with 10% FCS at 37° C., 5% $CO_2$. Cells were removed at 30 minute intervals for 150 minutes, mixed 1:1 with a Trypan blue solution (Sigma, 0.4% in 0.81% sodium chloride; 0.06% potassium phosphate dibasic) and 10 μL was transferred to a hemacytometer for cell counting at 100×. Visibly blue cells were counted as "dead."

Figure 12:
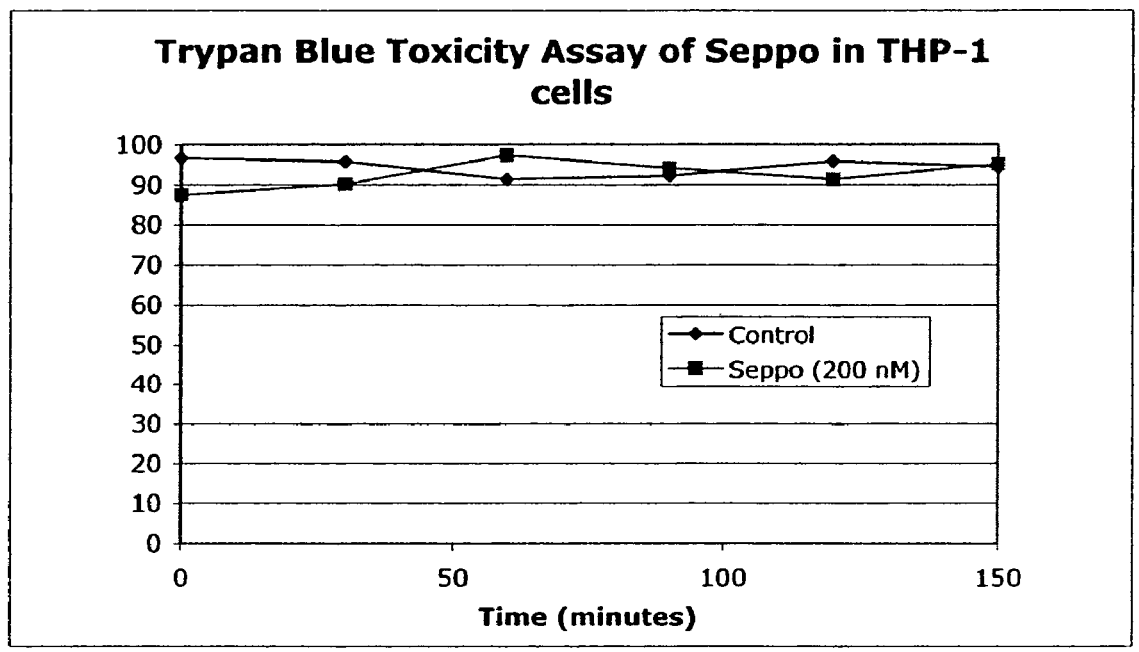
FIG. 12 depicts toxicity of 200 nM InstantLipo Sep-1toward THP-1 cells as measured by Trypan Blue Exclusion. Dark blue points are control THP-1 cells and the pink points are THP-1 cells incubated in the presence of 200 nM InstantLipo Sep-1.

Exemplary results examining the toxicity of InstantLipo Sep-1are presented in FIG. 12. and indicate that there was no difference in cell viability over a 2.5 hour period of exposure to either InstantLipo Sep-1or medium lacking dye. Similar results were obtained when cells were exposed to InstantLyso LLT-1.

Example 3

Cellular Localization of Dyes

A. LTI studies: Aliquots of THP-1 cells (Cell densities were $1\times10^6$ cells per mL) were exposed to either 100 nM InstantLyso LLT-1 in RPMI 1640 medium with 10% FCS at 37° C., 5% $CO_2$, both InstantLyso LLT-1 and 100 nM Lysotracker Red (Molecular Probes, Eugene Oreg.), or both InstantLyso LLT-1 and at a concentration of 75 nM. Mitotracker Red (Molecular Probes). In each case, medium is first pipetted off cells, then warmed medium containing dyes is added. The cell suspension is incubated for 30 minutes at 37° C. and examined by microscopy.

Only excess medium was removed from live cells in order to put on a coverslip with a silicone gasket well or to invert a coverslip-bottomed culture dish. Thus they remained in the same concentration of probe, except in fixed cells which of course were rinsed. Standard incubation times were set at 30 minutes except in experiments where we were looking at the speed of staining. All stained properly essentially within the time it takes to add, mix and visualize in the microscope (2-5 minutes). 30 minutes is a typical time in Molecular Probes protocols.

Figure 7:
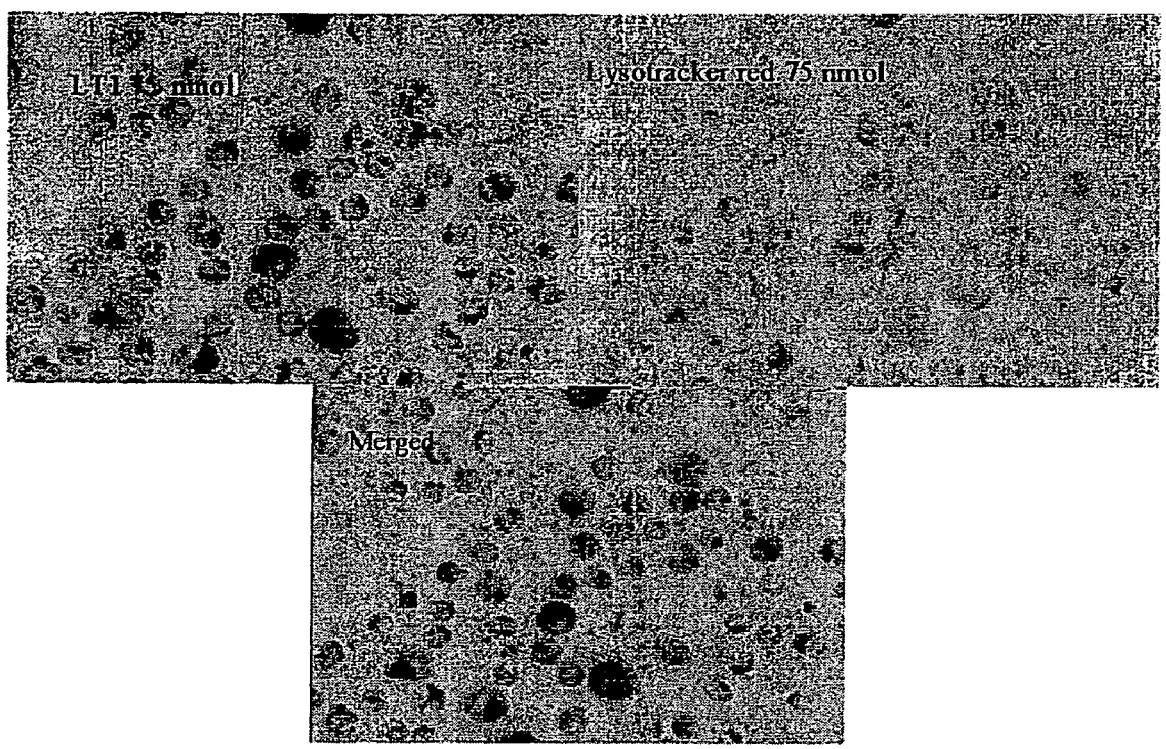
FIG. 7 depicts colocalization of LT-1 with Lysotracker red.

The THP-1 monocytic cells exposed to InstantLyso LLT-1 exhibited staining in punctate structures. The cells doubly labeled with InstantLyso LLT-1 and Lysotracker Red exhibited positive co-localization, indicating that InstantLyso LLT-1 appears to stain lysosomes, as shown in FIG. 7. The cells doubly labeled with InstantLyso LLT-1 and Mitotracker Red failed to exhibit such co-localization, confirming that InstantLyso LLT-1 does not localize in mitochondria. Colocalization of InstantLyso LLT-1 with Lysotracker red were performed under the following conditions: Live THP-1 Leukemic monocytes were grown in RPMI 1640 medium at 37C. and 5% $CO_2$ for 5 days. 2 mL of cells were allowed to adhere to a Biocoat (polylysine coated) glass bottomed cell culture plate for 30 minutes at 37C. The old medium was removed and 2 mLs of 37 C fresh media containing 1 00 nM InstantLyso LLT-1 (from 10 µM DMSO stock) and 100 nM Lysotracker Red (from 1 mM DMSO stock) was added. Cells were incubated at 37C for 30 minutes. And visualized with an inverted epifluorescence microscope at 600× using a blue/purple (450/50 ex and 510/50 em with D480 mirror) cube for InstantLyso LLT-1 and a green (560/50 ex and 646/40 em with D595 mirror). Exposure was automatic. Temperature was ambient.

InstantLyso LLT-1 also referred to as LewisLysosome-Tracker1(LLT-1) is a fluorescent weak base that accumulates inside acidic organelles such as lysosomes. InstantLyso LLT-1 is fixable and colocalizes with commercial probes (e.g. LysoTracker Red). The fluorescence of InstantLyso LLT-1 results from excitation of the photochemically resistant naphthalimide functional group. InstantLyso LLT-1 can be excited with a blue (460-490 nm) cube, a 488 nm line of Argon laser, or a purple (400-440 nm) cube. Concentration or light intensity may be reduced when excited with a purple cube. InstantLyso LLT-1 may be stored at $\geq 20°$ C. and away from light. Generally, InstantLyso LLT-1 may be used by first making a 10 µM stock solution, then adding DMSO to InstantLyso LLT-1 in vial to make a 1 mM stock. Finally, 10 µl of 1 mM stock is added to 1 ml of DMSO to make a 10 µM stock.

Figure 8:
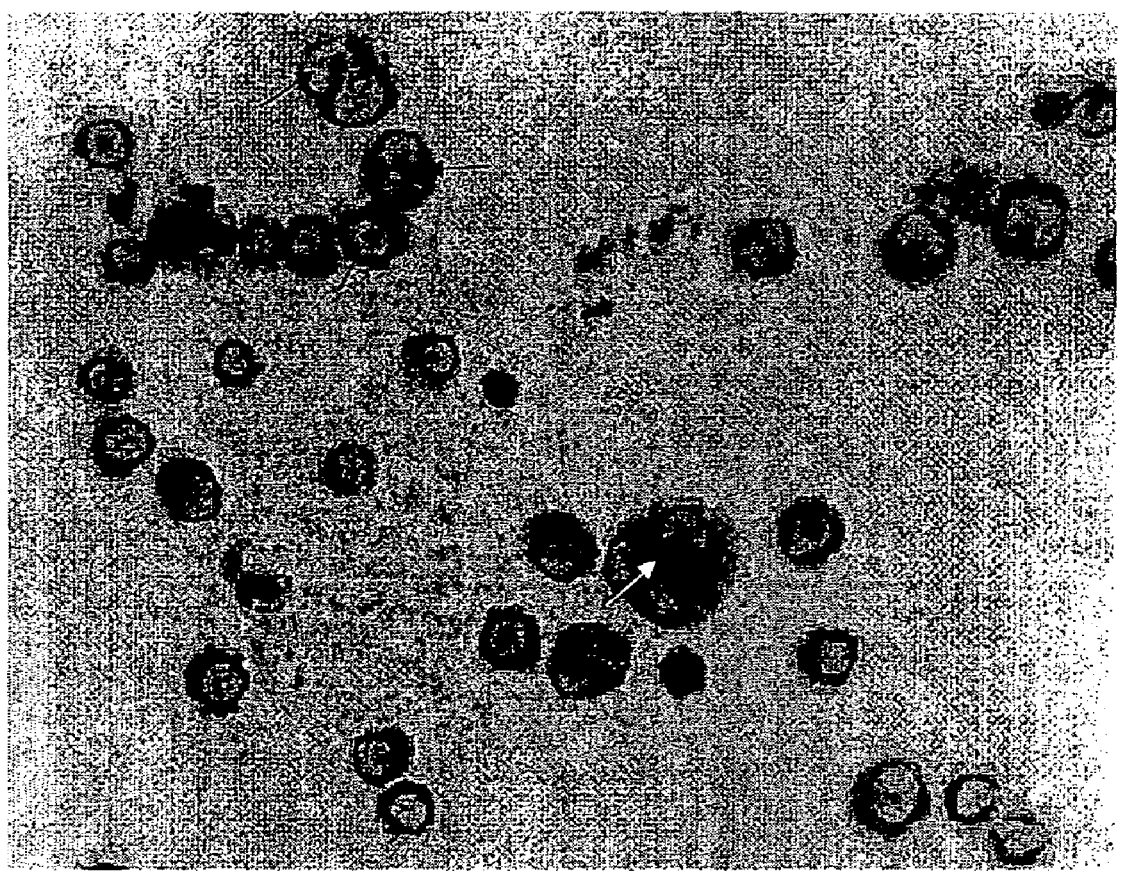
FIG. 8 depicts live THP-1 cells stained with 200 nM InstantLipo Sep-1for 20 minutes. Cells were visualized at 400×. Arrows point to typical examples of "donut" perinuclear structures believed to be microtubule organizing centers (MTOC).
Figure 9:
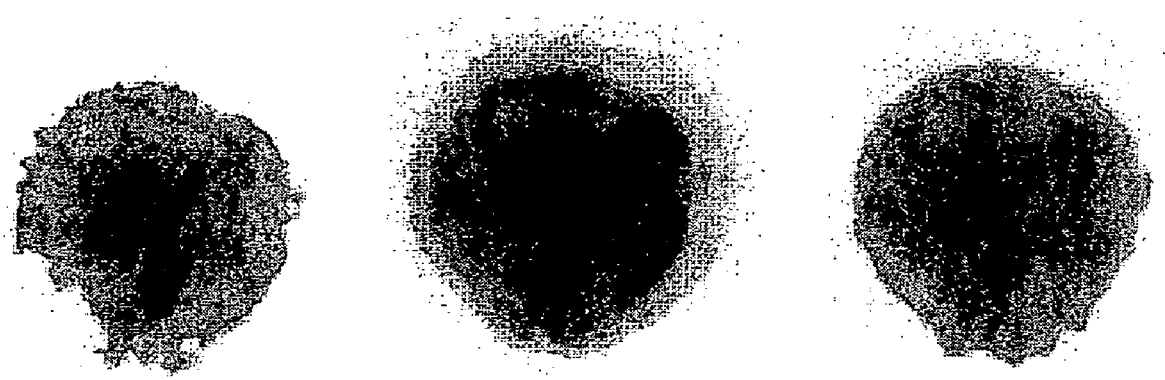
FIG. 9 depicts colocalization of InstantLipo Sep-1with Vybrant Lipid Raft probe. The left image (A) of InstantLipo Sep-1was captured under purple cube excitation. The center image (B) of Alexa 494-CTB emission was captured under green cube excitation. The right image (C) is a composite image is constructed in Adobe Photoshop. Areas of red represent Alexa 594 CTB Labeling Kit only, areas of green represent InstantLipo Sep-1only, and areas of yellow/orange are areas of overlap.

B. InstantLipo Sep-1 studies: Aliquots of either THP-1 cells or adherent human fibroblasts were exposed to either 200 nM InstantLipo Sep-1 in RPMI 1640 medium with 10% FCS at 37 C, 5% $CO_2$, both InstantLipo Sep-1 and Vybrant lipid raft kit (Molecular Probes, used according to the manufacturer's instructions), both InstantLipo Sep-1 and Mitotracker Red (Molecular Probes, used according to the manufacturer's instructions), or both InstantLipo Sep-1 and Lysotracker Red. Cells were incubated at 37° C. for at least 20 minutes. THP-1 cells stained with InstantLipo Sep-1 exhibited donut-like perinuclear structures as well as punctate structures, as shown in FIG. 8. Some of the punctate structures moved rapidly when observed by confocal microscopy in living cells. These structures co-localized with a Vybrant lipid raft staining kit in doubly labeled cells, as shown in FIG. 9. Conditions for colocalization are as follows: Live THP-1 Leukemic monocytes were grown in RPMI 1640 medium at 37 C and 5% $CO_2$ for 5 days. Cells were prepared according to the manufacturer's protocol for staining for lipid raft domains with Vybrant Alexa 594 kit (a cholera toxin-B/antibody labelling kit; Molecular Probes, http://www.probes.com/media/pis/mp34403.pdf ). At the initial step in the process, the cells were incubated with 200 nM InstantLipo Sep-1(from 20µM DMSO stock) for 10 min, 37C in RPMI medium. Thus the InstantLipo Sep-1 was carried through the entire Vybrant staining process. The cells were visualized at 1000× as before for InstantLipo Sep-1 and Lysotracker Red, but the cells were placed under a coverslip on a slide and visualized under the 1000× oil immersion objective at ambient temperature. Superimposition was carried out in Photoshop. Yellow areas are colocalized.

Figure 17:
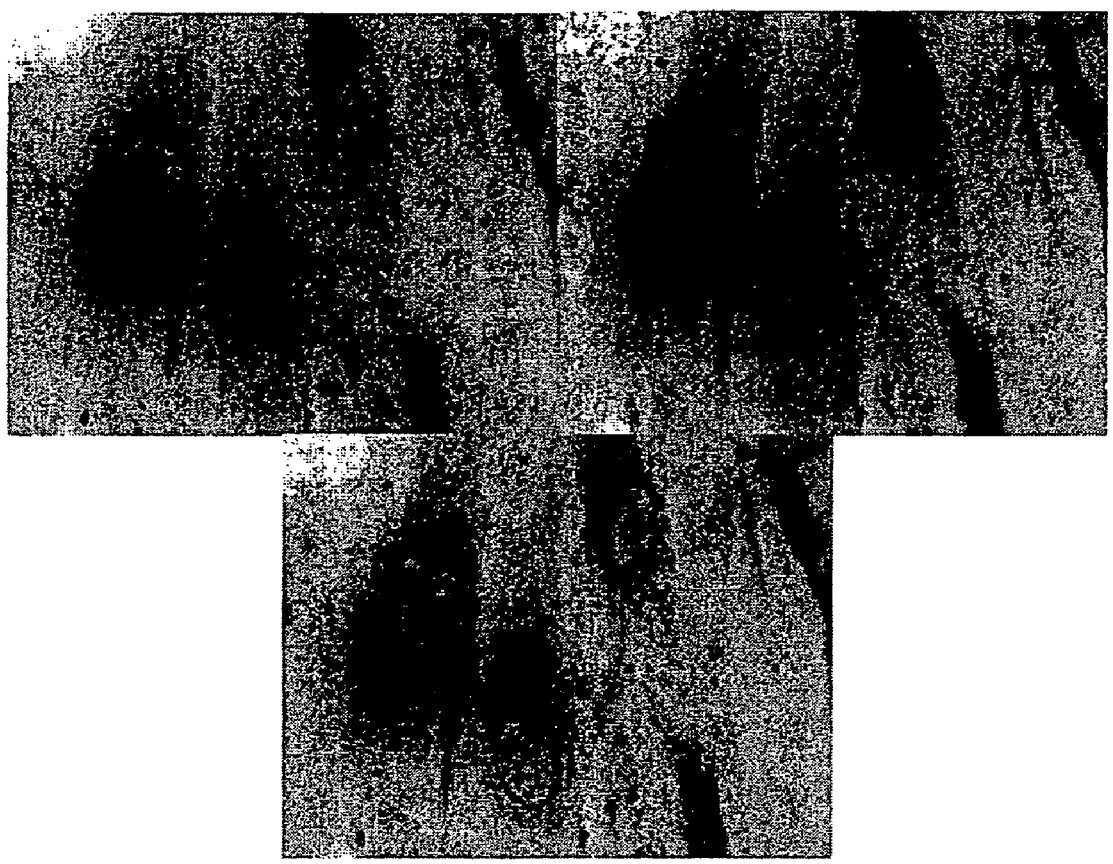
FIG. 17 depicts InstantGolgi McN-1 and BODIPY TR $C_5$ ceramide complexed to BSA with partial Golgi localization. The upper left image was captured under purple cube excitation with 1000× magnification and shows the fluorescence of InstantGolgi McN-1. The upper right image was captured under green cube excitation with 1000× magnification and shows the fluorescence of BODIPY TR $C_5$ ceramide complexed to BSA. The lower image is the merged fluorescence of both probes.

Double staining with either Mitotracker Red confirmed that InstantLipo Sep-1 was not staining mitochondria, whereas double staining with Lysotracker Red confirmed that InstantLipo Sep-1 was not exclusively staining lysosomes. This is not surprising since some cholesterol rich caveolar domains typically end up fusing with lysosomes. However it is clear that its distribution is distinct from that of acidic organelles. The chemical structure would preclude InstantLipo Sep-1 from being accumulated in acidic organelles, however, it may be accumulated in their membranes. The perinuclear donut stained structures may be the microtubule organizing center (MTOC), consistent with co-localization in raft domains, since the MTOC is associated with microtubule-linked transport of caveolar vesicles to and from the membrane to the trans Golgi network (D. I. Mundy, T. Machleidt, Y. S. Ying, R. G. Anderson and G. S. Bloom, J Cell Sci 115 (2002) 4327-39). These results are consistent with results from additional dual staining experiments were carried out to investigate localization of InstantLipo Sep-1 to the Golgi. Foreskin fibroblasts were grown on coverslips for 4 days in EMEM. Cells were treated with both InstantLipo Sep-1 and BODIPY TR $C_5$ ceramide complexed to BSA, as seen in FIG. 17 (Molecular Probes Kit #B34400, used according to manufacturer's direction. The results indicated partial colocalization with the Golgi.

Figure 10:
FIG. 10 depicts InstantLipo Sep-1staining of a live foreskin fibroblast Human foreskin fibroblasts were grown for one week in EMEM at 37° C. and 5% $CO_2$ on glass coverslips. Cells were stained as before with 200 nM InstantLipo Sep-1and visualized at 1000×.
Figure 11:
FIG. 11 depicts InstantLipo Sep-1in 4% paraformaldehyde-fixed fibroblasts treated for 12 hours with U 18666A.

Both live and 4% paraformaldehyde fixed human foreskin fibroblasts were exposed to 200 nM InstantLipo Sep-1 at 37° C. for more than 20 minutes, as shown in FIGS. 10 and 11. Punctate structures similar to those observed with filipin-stained fixed cells were observed (X. Sun, D. L. Marks, W. D. Park, C. L. Wheatley, V. Puri, J. F. O'Brien, D. L. Kraft, P. A. Lundquist, M. C. Patterson, R. E. Pagano and K. Snow, Am J Hum Genet 68 (2001) 1361 -72).

Figure 14:
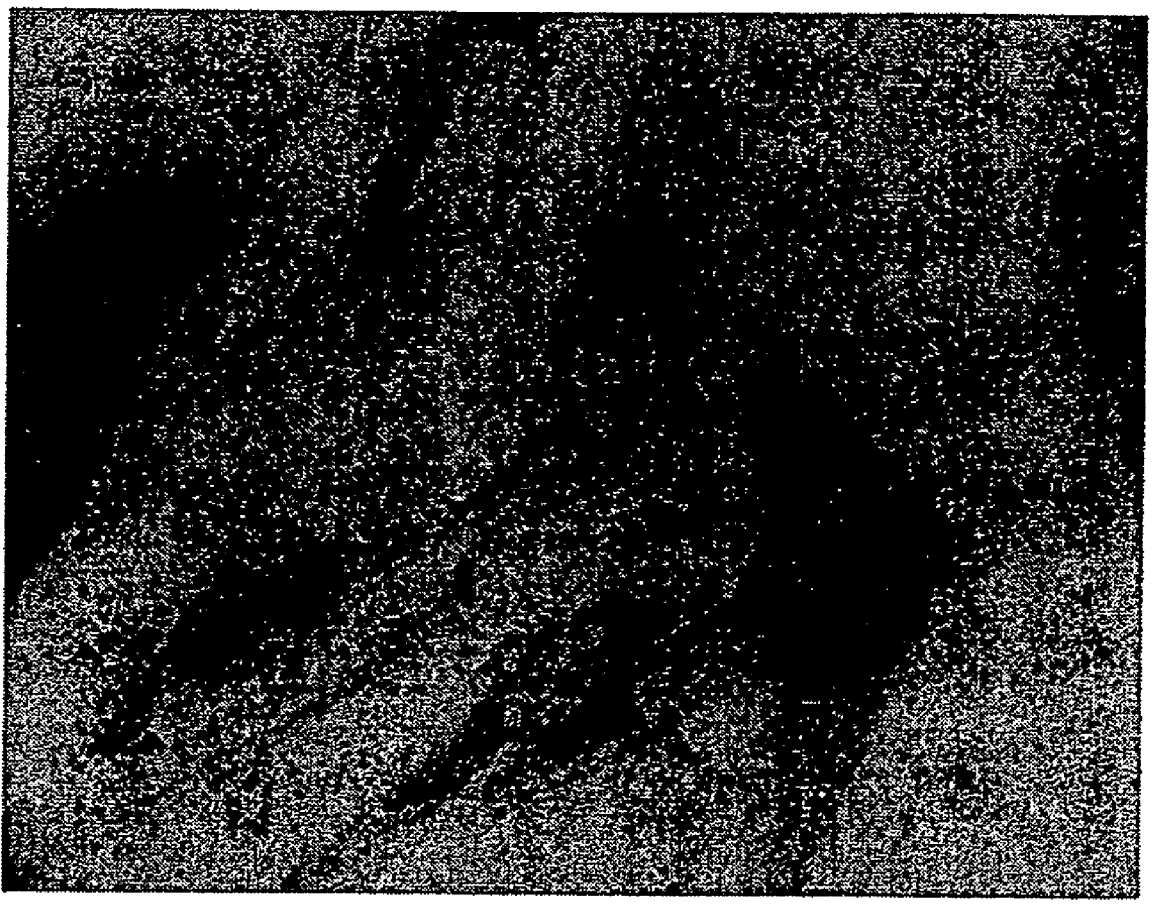
FIG. 14 depicts Fibroblasts stained with InstantLipo Sep-1and exposed to 3 μg/ml U 18666A

Similarly, 3 µg/mL from $H_2O$ stock of aminoesterol U18666A (Calbiochem)) is often used with fibroblasts to inhibit intracellular cholesterol transport and leads to accumulation of cholesterol in nuclear regions (C. F. Roff, E. Goldin, M. E. Comly, A. Cooney, A. Brown, M. T. Vanier, S. P. Miller, R. O. Brady and P. G. Pentchev, Dev Neurosci 13 (1991) 315-9). Foreskin fibroblasts were grown on coverslips for 1 day in EMEM. Medium was removed and replaced with 2 mL fresh EMEM to ensure consistent treatment as cells that were treated with U18666A. Cells were incubated at 37° C. and 5% $CO_2$ overnight. Medium was removed and replaced with 2 mL EMEM containing 200 nM InstantLipo Sep-1. Cells were then incubated at 37° C. and 5% $CO_2$ for 30 minutes to allow dye to load. Cells were imaged using an epifluorescence microscope at 1000× magnification while excited with a purple cube. Fibroblasts stained with InstantLipo Sep-1 and exposed to 3 µg/ml U18666A exhibited enhanced perinuclear staining relative to cells stained just with InstantLipo Sep-1, consistent with localization of InstantLipo Sep-1 in cholesterol-rich raft domains, as seen in FIG. 14.

One of the major disadvantages (see Table 1) of using filipin to stain cholesterol-rich domains is its extreme cytotoxicity. In order to assess InstantLipo Sep-1's toxicity a standard Trypan blue exclusion assay for cell death was carried out on THP-1 cells (due to the ease of aliquot removal). As seen in FIG. 12, InstantLipo Sep-1 showed no significant cytotoxicity at 200 nM over 150 minutes. This important result indicates that trafficking of microdomains and cholesterol-rich organelles can be monitored in live cells. It further suggests that treatments/drugs which might lower cellular cholesterol metabolism/uptake could be monitored by high throughput assays using InstantLipo Sep-1 as a probe.

Some notable features of InstantLipo Sep-1 which distinguish it from other modes of lipid raft visualization procedures and other patented naphthalimide probes are: that (1) InstantLipo Sep-1 is very fluorescent in both water and membrane milieu. (2) InstantLipo Sep-1 is non-toxic. (3) InstantLipo Sep-1 is photostable. (4) InstantLipo Sep-1 stains internal live cellular structures within 15 seconds, unlike other probes which need to be taken in by pinocytosis or endocytosis. (5) InstantLipo Sep-1is fixable with 4% paraformaldehyde and still fluorescent and still well-localized. (6) InstantLipo Sep-1localizes with filipin but also stains distinct domains apart from pathological cholesterol deposits observed with Filipin. (7) One structure which may be stained intensely by InstantLipo Sep-1is the MTOC (microtubule organizing center) near the nucleus. See "cheerio" structure in FIG. 8. It is perhaps the only membrane-permeable probe to do this especially for live cells. (8) InstantLipo Sep-1may bind to sterol or simple liquid-ordered membrane domains. Further, InstantLipo Sep-1may specifically label the protein caveolin which is a sterol-binding protein. This could explain its association with rapidly trafficking vesicles [13] as well as the MTOC (which is a "sink" for caveolar derived vesicles).

Figure 18:
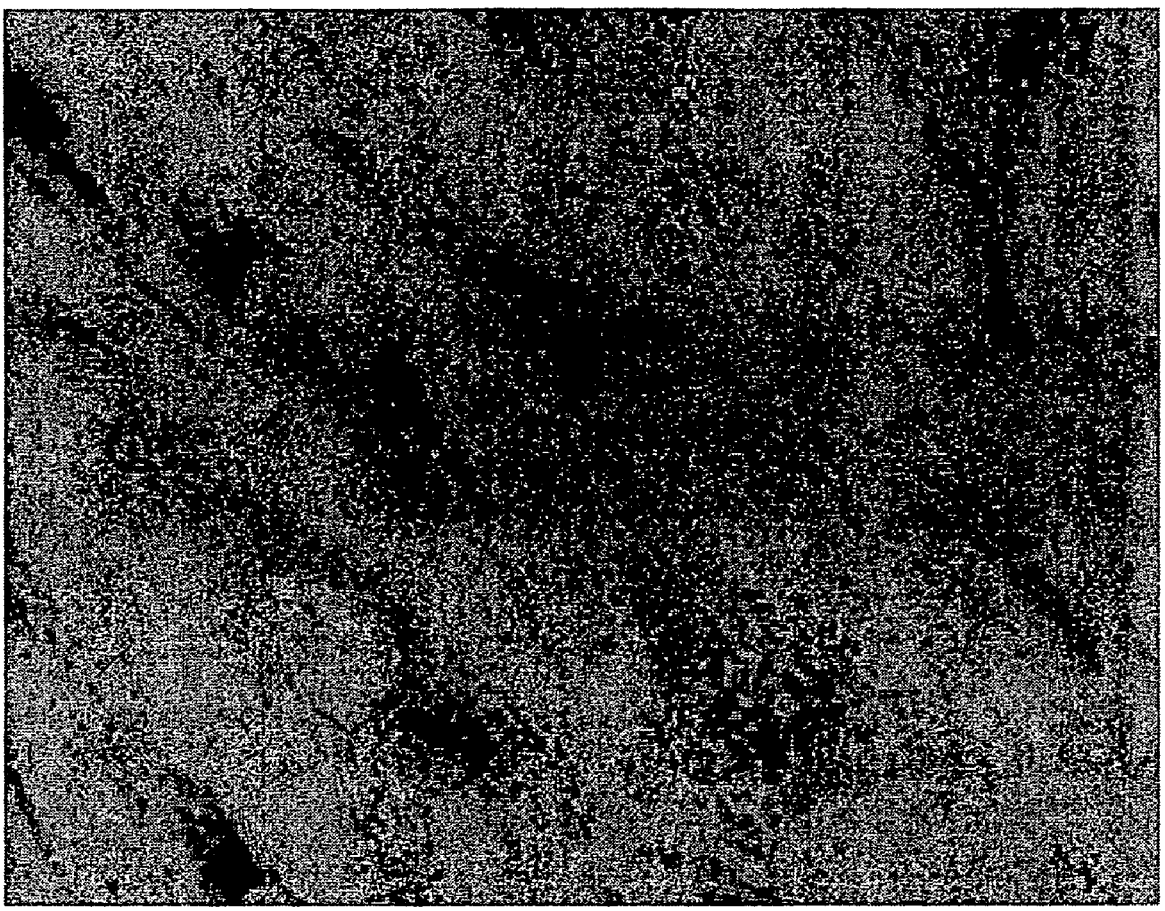
FIG. 18 depicts InstantGolgi McN-1 and U18666A uptake. Cells were imaged using an epifluorescence microscope at 1000× magnification while excited with a purple cube.

Accordingly, the uses of InstantLipo Sep-1include the following: (a) Microscopic or plate diagnostic test for Neimann-Pick type C in cultured patient cells. This niche is now filled by Filipin. (b) High-throughput cell culture assays for potential cholesterol-lowering drugs (e.g. statin-type). (c) Pathology microscopic visualization of atherschlerotic plaques autopsy or biopsy. Since InstantLipo Sep-1is non-toxic, it could possibly could be used in live patients to visualize atherosclerotic lesions by 2-photon fluorescence C. InstantGolgi McN-1 Studies Foreskin fibroblasts were grown on coverslips for 3 days in EMEM. Medium was removed and replaced with 2 mL EMEM containing 3µg/mL U18666A. Cells were incubated at 37° C. and 5% $CO_2$ overnight. Medium was removed and replaced with 2 mL EMEM containing 150 nM InstantGolgi McN-1. Cells were then incubated at 37° C. and 5% $CO_2$ for 30 minutes to allow dye to load. Cells were imaged using an epifluorescence microscope at 1000x magnification while excited with a purple cube, as seen in FIG. 18. Results indicated more punctate bright spots in cells after inhibition. This is consistent with the staining of more numerous and pathological cholesterol-rich domains and vesicles. This is expected upon U18666A treatment, since it disrupts intracellular cholesterol transport. The cellular changes seen mimic those of Neimann-Pick type C disease and InstantLipo Sep-1and InstantGolgi McN-1 could potentially be used as diagnostic reagents for this disorder. The difference in cellular appearance was not quite so pronounced with InstantGolgi McN-1 as it was with InstantLipo Sep-1. Thus there seems to be a preference of InstantGolgi McN-1 for Golgi and MTOC staining, InstantLipo Sep-1for cholesterol-rich inclusions though there is overlap.

Figure 15:
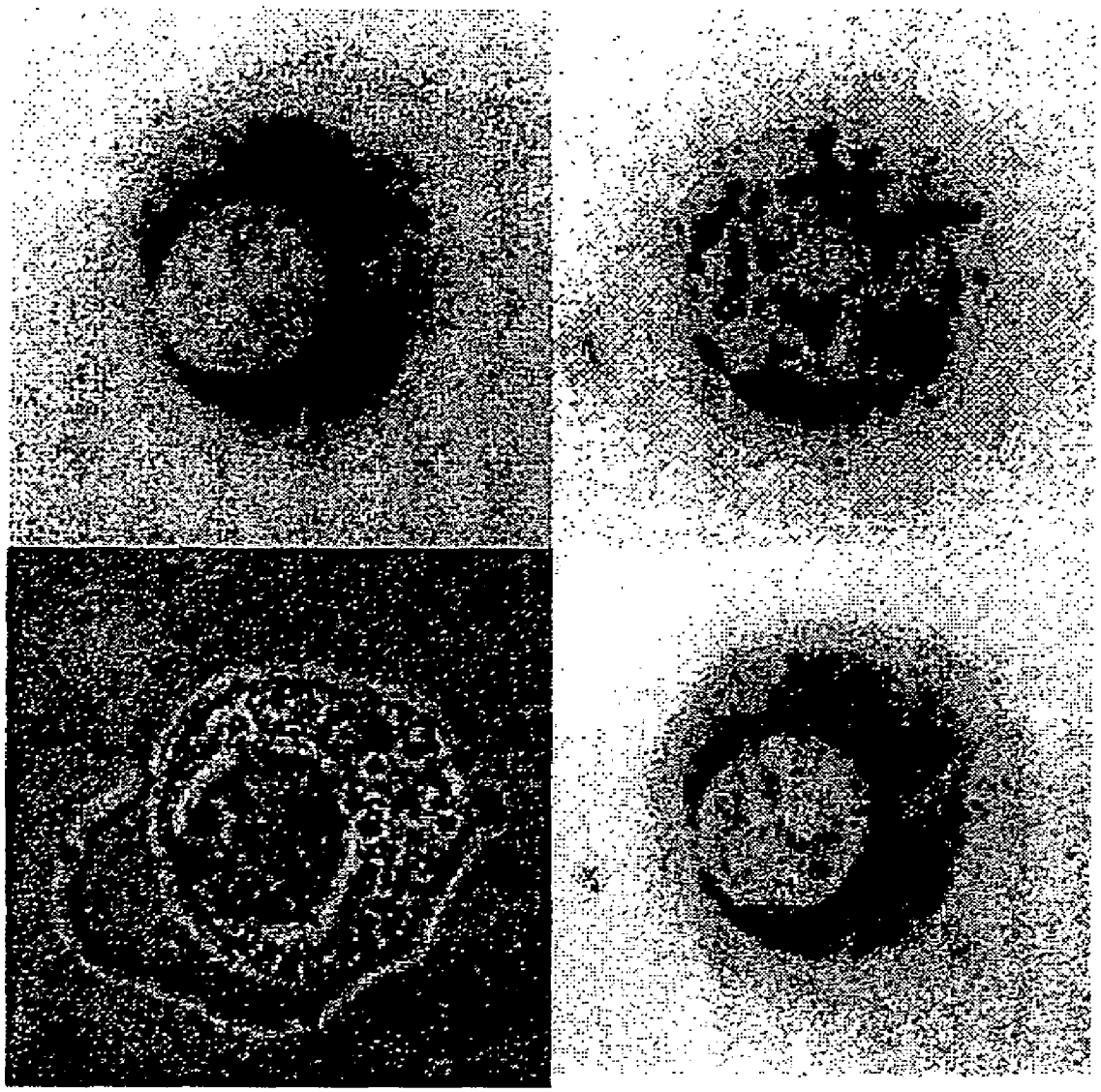
FIG. 15 depicts THP-1 monocytes loaded with 150 nM InstantGolgi McN-1 and labeled with Molecular Probes Vybrant® Alexa Fluor® 594 Lipid Raft Labeling Kit.

THP-1 monocytes were loaded with 150 nM InstantGolgi McN-1 and labeled with Molecular Probes Vybrant® Alexa Fluor® 594 Lipid Raft Labeling Kit as seen in FIG. 15. The upper left image of InstantGolgi McN-1 was captured under purple cube excitation. The upper right image of Molecular Probes Vybrant® Lipid Raft Labeling Kit was captured under green cube excitation. The lower left image is a visual image. The lower right image is a composite image constructed in Adobe Photoshop by pasting the green channel of the first image into the green channel of the visible image and the red channel of the second image into the red channel of the visible image. Areas of red represent Molecular Probes Vybrant® Lipid Raft Labeling Kit only, areas of green represent InstantGolgi McN-1 only, and areas of yellow are areas of overlap.

Figure 13:
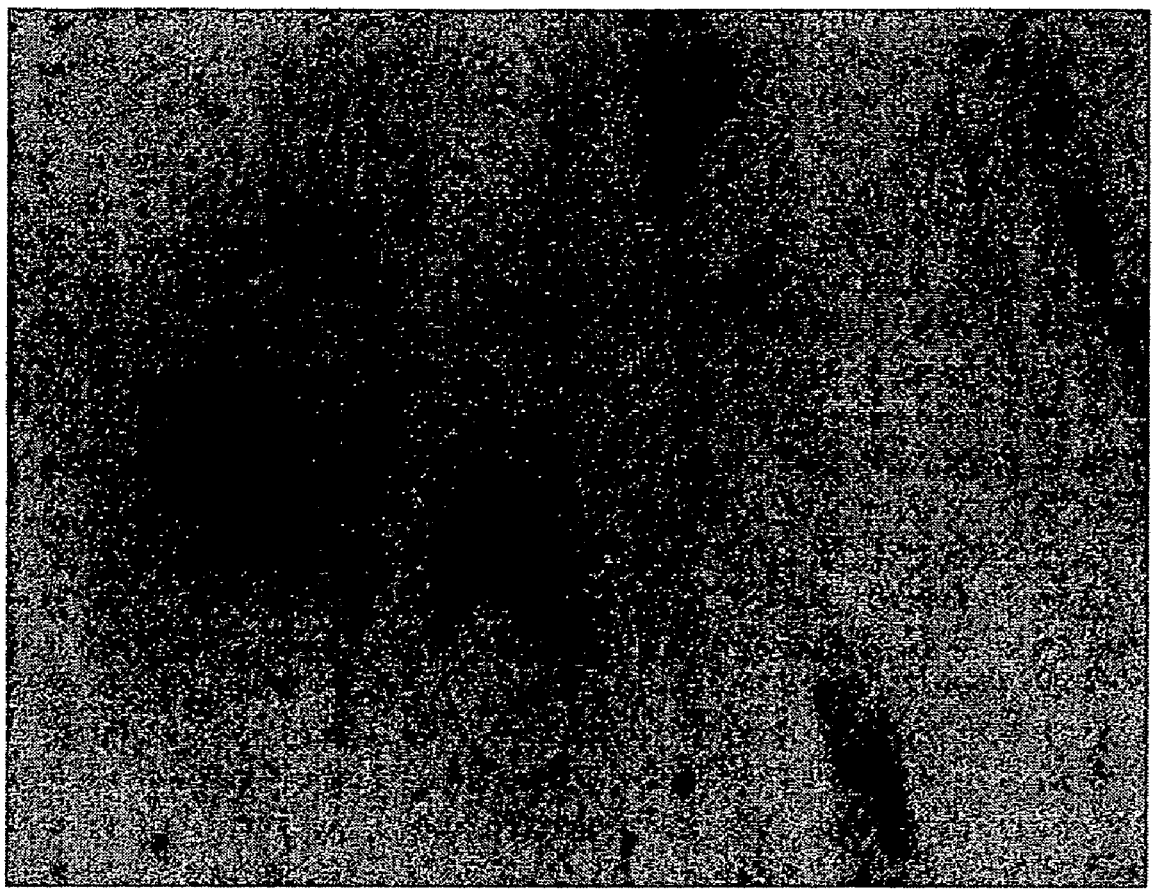
FIG. 13 depicts InstantGolgi McN-1 localization in the Golgi as visualized with red BODIPY

The inventors have firmed up localizations for InstantGolgi McN-1 and InstantLipo Sep-1. Both InstantLipo Sep-1and InstantGolgi McN-1 Colocalize with the Golgi apparatus. The Golgi was visualized with red BODIPY labeled ceramide (Molecular Probes). This localization is important because the Golgi is the "clearinghouse" for cholesterol metabolism and caveolar transport vesicles (with raft-like high cholesterol and sphingolipid). Mc Nitt, however, appears to have better visualization than InstantLipo Sep-1, as shown in FIG. 13.

Further, InstantGolgi McN-1 and InstantLipo Sep-1can visualize pathological cholesterol metabolism. Normal human fibroblasts were incubated with U18666A, an aminosterol which blocks cholesterol transport in cells (Roff, C. F., E. Goldin, et al. (1991). "Type C Niemann-Pick disease: use of hydrophobic amines to study defective cholesterol transport." *Dev Neurosci* 13(4-5): 315-9). Bright enhanced perinuclear "blobs" which are cholesterol-rich deposits are clearly visible. The images are much like those of Filipin which can only be used on fixed dead cells. These cells, however are live. This opens the potential for diagnostic uses and high throughput screening of cholesterol lowering drugs. In this application, it seems InstantLipo Sep-1works even better than InstantGolgi McN-1, as seen in FIG. 14.

Figure 16:
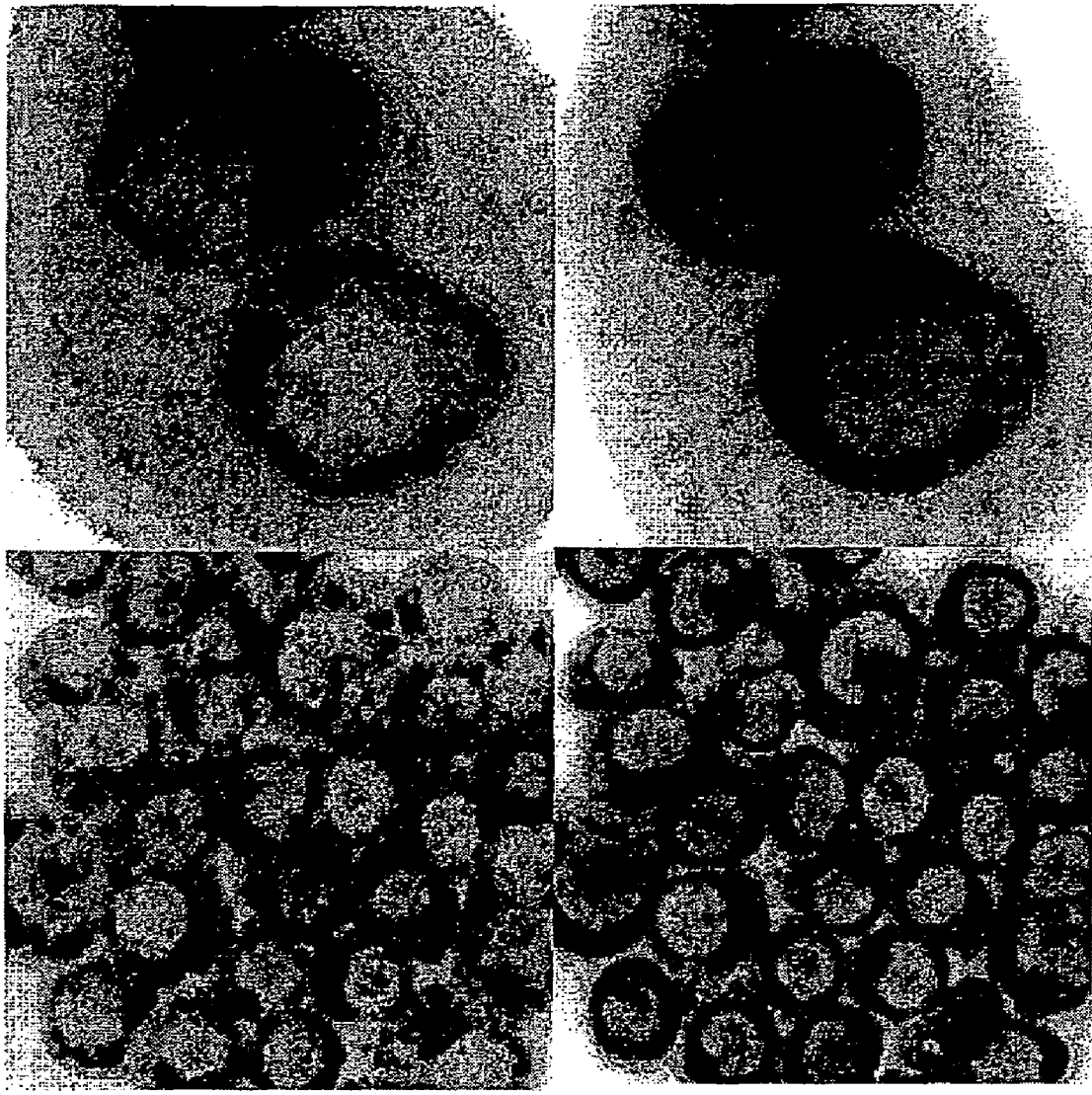
FIG. 16 depicts compartitive visualization using 75 nM of LysoTracker Red and 150 nM InstantGolgi McN-1

Comparative studies of 75 nM Lysotracker Red and 150 nM of InstantGolgi McN-1 confirmed that InstantGolgi McN-1, as seen in FIG. 16 was not labeling lysosomes or mitochondria. The experiments showed limited colocalization with lysosomes and mitochondria. This suggests that a different physical structure is labeled specifically by McNitt. The other experiments suggest McNitt labels cholesterol-rich raft-like domains and in particular, the Golgi apparatus. McNitt at 200 nM was incubated with live THP-1 cells. Lysotracker and Mitotracvker from Molecular Probes were used according to manufacturer's instructions as previously outlined.

Figure 19:
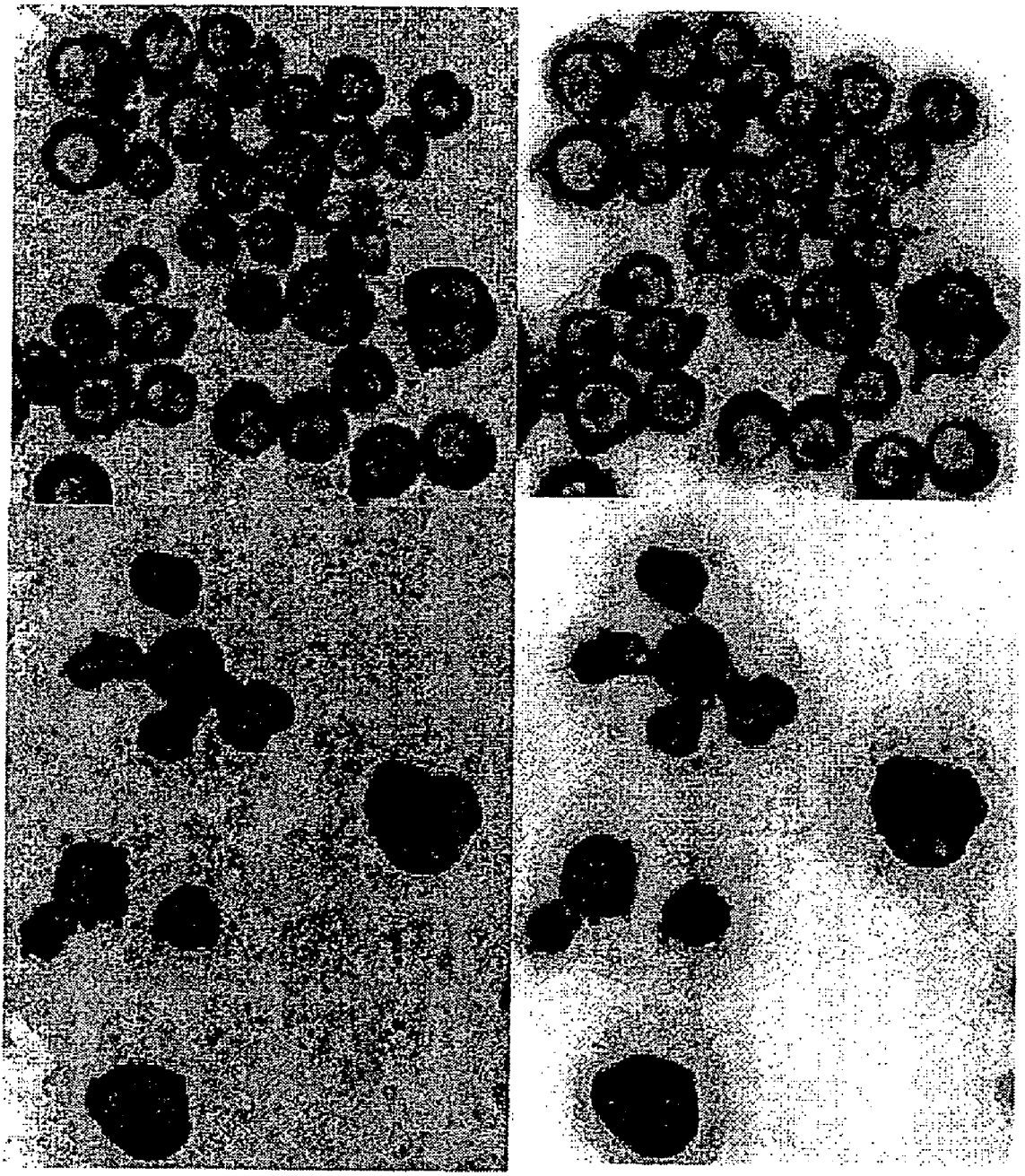
FIG. 19 depicts comparative studies of 50 nM MitoTracker Red and 150 nM InstantGolgi McN-1.

Comparative studies of 50 nM MitoTracker Red and 150 nM InstantGolgi McN-1 are shown in FIG. 19.

The dyes of the present invention hold up well to photobleaching relative to the time needed to take most fluorescence shots (a few seconds). INSTANTLYSO LLT-1 holds up much better than the others, possibly due to the "friendlier" chemical environment of the acidic lysosomes as compared to the membrane domains favored by InstantLipo Sep-1and InstantGolgi McN-1, as seen in FIGS. 25 A, B, C and D.

Figure 22:
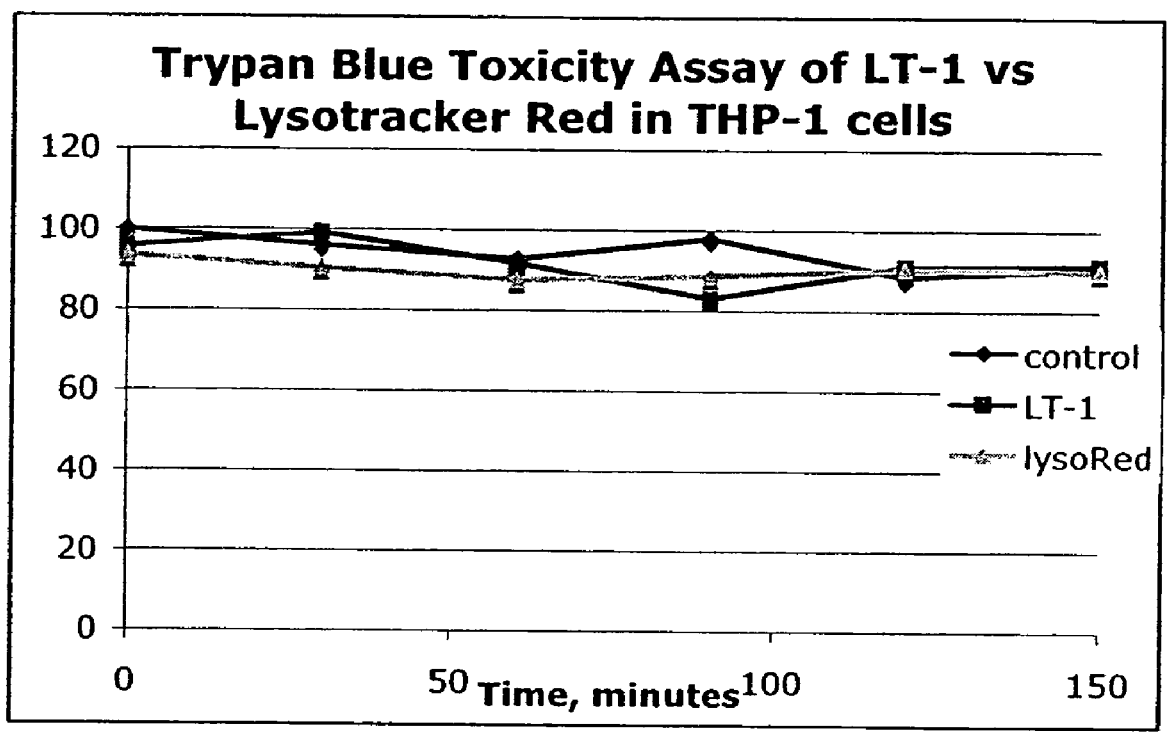
FIG. 22 depicts Trypan Blue toxicity assay of LT-1 versus LysoTracker Red in THP-1 cells.
Figure 23:
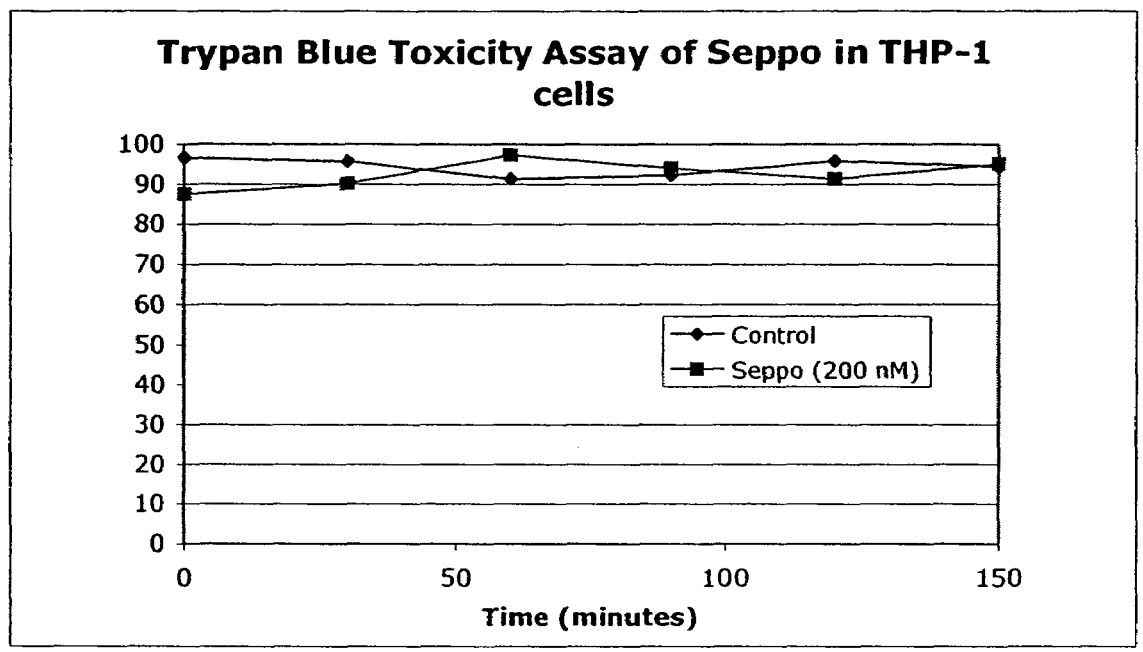
FIG. 23 depicts Trypan Blue toxicity assay of InstantLipo Sep-1in THP-1 cells.
Figure 24:
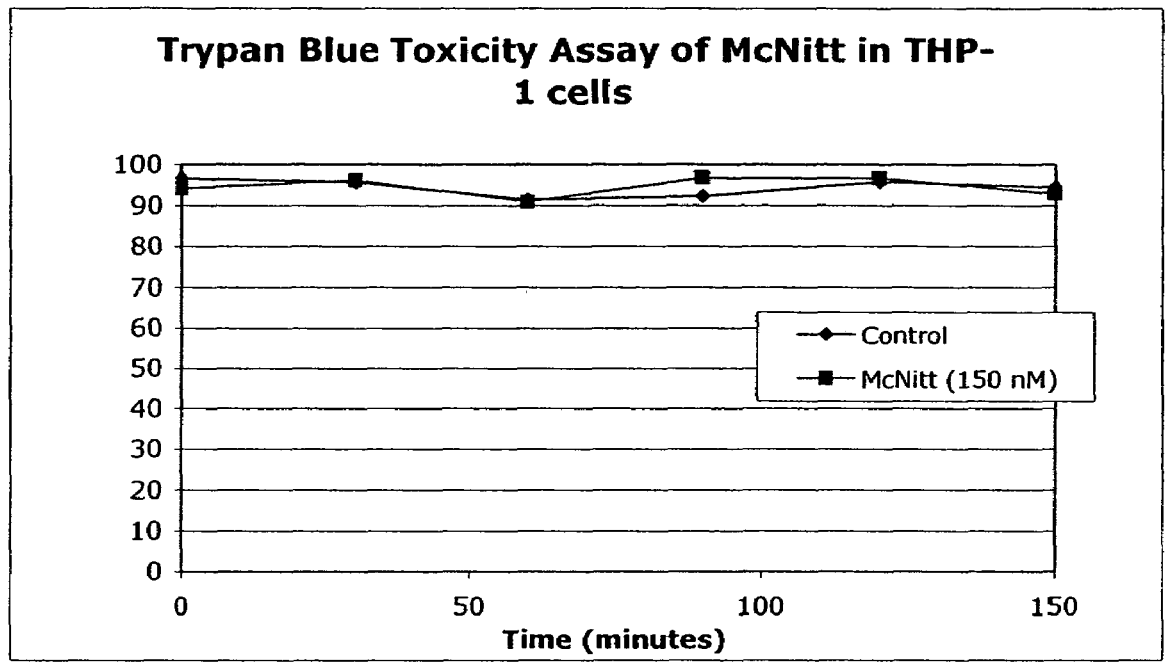
FIG. 24 depicts Trypan Blue toxicity assay of InstantGolgi McN-1 in THP-1 cells.
Figure 25A:
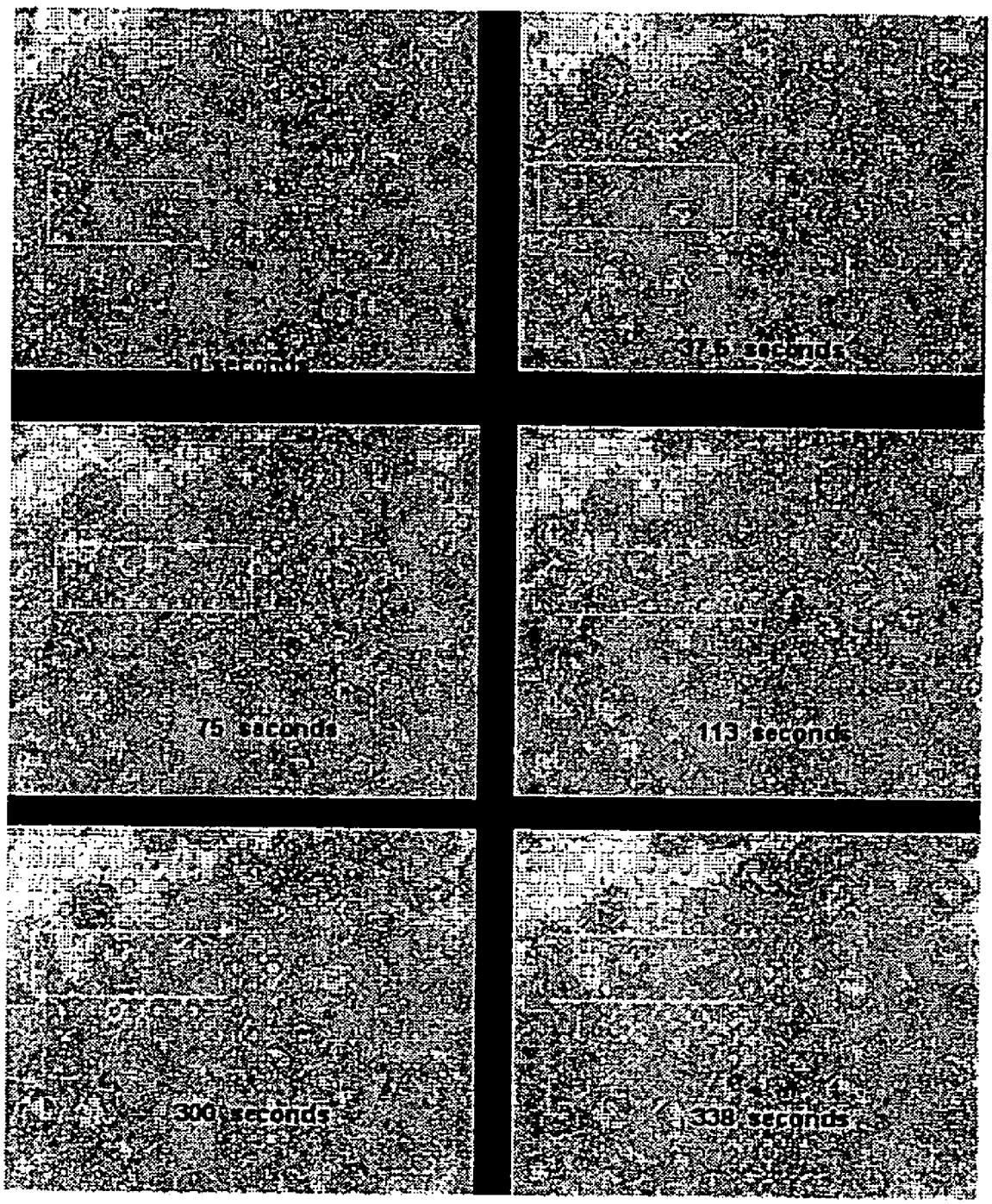
FIG. 25 depicts (A) InstantLyso LLT-1 at 75 nM in THP-1 cells. Exposures were taken every 30 seconds (with consistent CCD exposure length 7.5 seconds) with blue excitation cube (490 nm maximum).; (B) InstantGolgi McN-1 at 200 nm in THP-1 cells. Exposures were taken with consistent CCD exposure length with purple excitation cube.; (C) InstantLipo Sep-1at 200 nm in THP-1 cells. Exposures were taken with consistent CCD exposure length with purple excitation cube; and (D) Lysotracker Red at 75 nM in THP-1 cells. Exposures were taken every 5 seconds (with consistent CCD exposure length) with green excitation cube. Unretouched, unprocessed images.
Figure 25B:
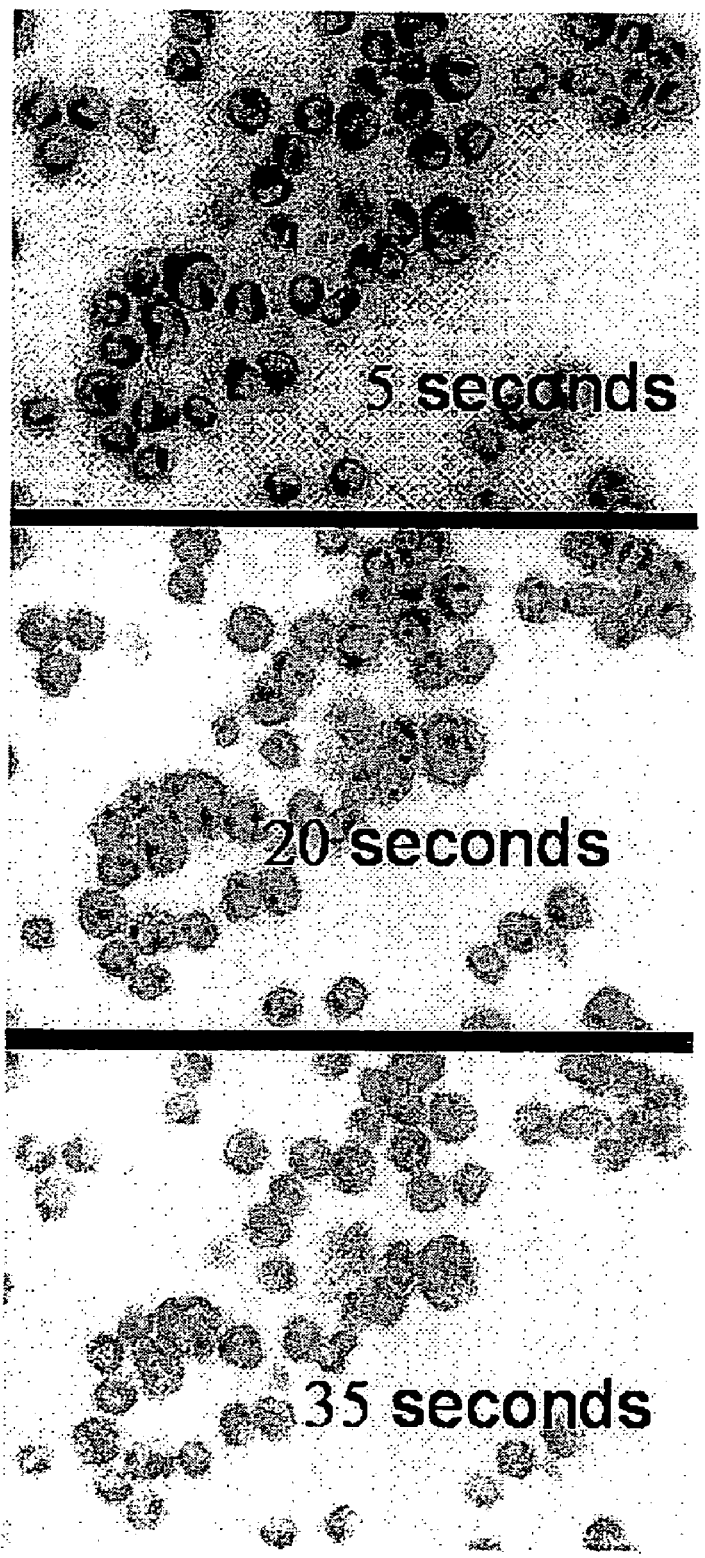
Figure 25C:
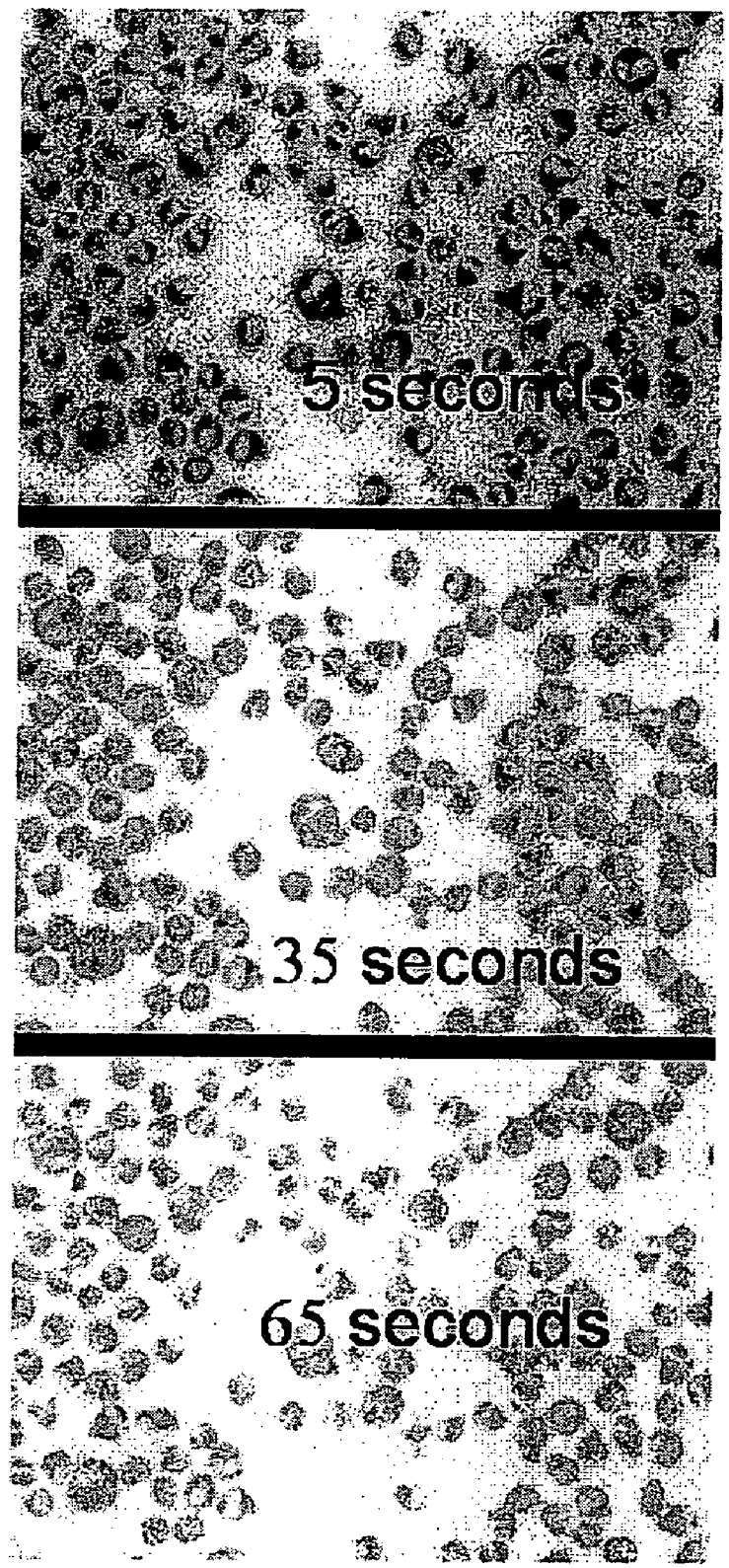
Figure 25D:
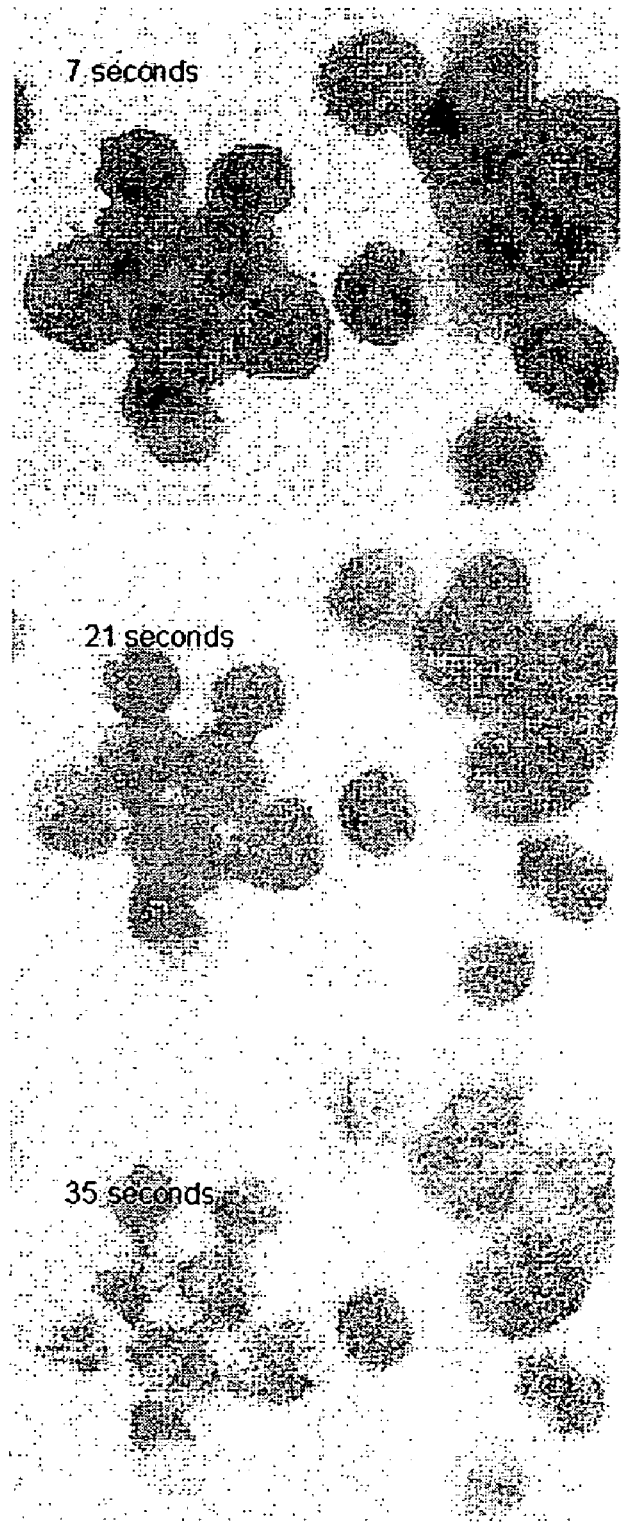

Viability on InstantGolgi McN-1 (see FIGS. 22, 23, and 24) is the same as the others dyes of the present invention; InstantGolgi McN-1 like others described here has no significant cytotoxicity. Furthermore, the excitation/emission spectra is also very much like the others.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES (1) T. N. Raju, Lancet 355 (2000) 416.
(2) S. B. Sato, K. lshii, A. Makino, K. Iwabuchi, A. Yamaji-Hasegawa, Y. Senoh, I. Nagaoka, H. Sakuraba and T. Kobayashi, J Biol Chem 279 (2004) 23790-6.
(3) R. D. Singh, V. Puri, J. T. Valiyaveettil, D. L. Marks, R. Bittman and R. E. Pagano, Mol Biol Cell 14 (2003) 3254-65.
(4) K. Simons and R. Ehehalt, J Clin Invest 110 (2002) 597-603.

(5) P. A. Orlandi and P. H. Fishman, J Cell Biol 141 (1998) 905-15.
(6) H. Shogomori and A. H. Futerman, J Neurochem 78 (2001) 991-9.
(7) M. L. Torgersen, G. Skretting, B. van Deurs and K. Sandvig, J Cell Sci 114 (2001) 3737-47.
(8) J. E. Schnitzer, P. Oh, E. Pinney and J. Allard, J Cell Biol 127 (1994) 1217-32.
(9) F. Schroeder, A. M. Gallegos, B. P. Atshaves, S. M. Storey, A. L. Mcintosh, A. D. Petrescu, H. Huang, O. Starodub, H. Chao, H. Yang, A. Frolov and A. B. Kier, Exp Biol Med (Maywood) 226 (2001) 873-90.
(10) C. Dietrich, L. A. Bagatolli, Z. N. Volovyk, N. L. Thompson, M. Levi, K. Jacobson and E. Gratton, Biophys J 80 (2001) 1417-28.
(11) D. A. Brown, Proc Natl Acad Sci USA 98 (2001) 10517-8.
(12) L. W. Turtinen, A. Assimacopoulos and A. T. Haase, Microb Pathog 7 (1989) 135-45.
(13) D.l. Mundy, T. Machleidt, Y. S. Ying, R. G. Anderson and G. S. Bloom, J Cell Sci 115 (2002) 4327-39.
(14) V. Puri, J. R. Jefferson, R. D. Singh, C. L. Wheatley, D. L. Marks and R. E. Pagano, J Biol Chem 278 (2003) 20961-70.
(15) D. K. Sharma, J. C. Brown, A. Choudhury, T. E. Peterson, E. Holicky, D. L. Marks, R. Simari, R. G. Parton and R. E. Pagano, Mol Biol Cell 15 (2004) 3114-22.
(16) C. F. Roff, E. Goldin, M. E. Comly, A. Cooney, A. Brown, M. T. Vanier, S. P. Miller, R. O. Brady and P. G. Pentchev, Dev Neurosci 13 (1991) 315-9.
(17) X. Sun, D. L. Marks, W. D. Park, C. L. Wheatley, V. Puri, J. F. O'Brien, D. L. Kraft, P. A. Lundquist, M. C. Patterson, R. E. Pagano and K. Snow, Am J Hum Genet 68 (2001) 1361-72.

What is claimed is:
1. A compound having the structure:

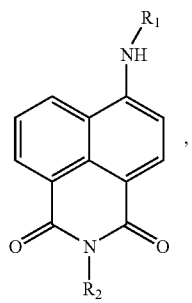

wherein $R_1$ is

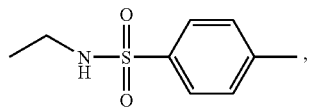

and, wherein $R_2$ is a member selected from $(CH_2)_5CH_3$, $(CH_2)_6CH_3$, and $(CH_2)_7CH_3$, or a pharmaceutically acceptable salt thereof.

2. A pharmaceutical composition comprising:
a compound having the structure:

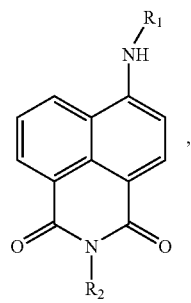

wherein $R_1$ is

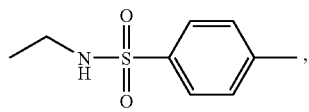

and wherein $R_2$ is a member selected from $(CH_2)_5CH_3$, $(CH_2)_6CH_3$, and $(CH_2)_7CH_3$, or a pharmaceutically acceptable salt thereof, and,
a pharmaceutically-acceptable carrier.

* * * * *